US011998658B2

(12) United States Patent
Jeong

(10) Patent No.: US 11,998,658 B2
(45) Date of Patent: Jun. 4, 2024

(54) INJECTABLE POROUS HYDROGELS

(71) Applicant: University of New Hampshire, Durham, NH (US)

(72) Inventor: Kyung Jae Jeong, Durham, NH (US)

(73) Assignee: University of New Hampshire, Durham, NH (US)

( * ) Notice: Subject to any disclaimer, the term of this patent is extended or adjusted under 35 U.S.C. 154(b) by 389 days.

(21) Appl. No.: 16/786,312

(22) Filed: Feb. 10, 2020

(65) Prior Publication Data

US 2020/0254142 A1 Aug. 13, 2020

Related U.S. Application Data

(60) Provisional application No. 62/802,816, filed on Feb. 8, 2019.

(51) Int. Cl.

| | |
|---|---|
| ***A61L 27/22*** | (2006.01) |
| ***A61L 27/36*** | (2006.01) |
| ***A61L 27/38*** | (2006.01) |
| ***A61L 27/52*** | (2006.01) |

(52) U.S. Cl.

CPC ......... *A61L 27/222* (2013.01); *A61L 27/3687* (2013.01); *A61L 27/3834* (2013.01); *A61L 27/52* (2013.01); *A61L 2400/06* (2013.01)

(58) Field of Classification Search

CPC ............... A61L 27/222; A61L 27/3687; A61L 27/3834; A61L 27/52; A61L 2400/06; A61L 27/38; A61L 27/50; A61L 27/56

See application file for complete search history.

(56) References Cited

U.S. PATENT DOCUMENTS

| | | | | |
|---|---|---|---|---|
| 2014/0170224 A1* | 6/2014 | Li | A61K 9/5057 | 424/492 |
| 2016/0008475 A1* | 1/2016 | Alsberg | A61K 47/42 | 514/774 |
| 2016/0024461 A1* | 1/2016 | Sun | C08J 3/24 | 435/68.1 |
| 2019/0070338 A1* | 3/2019 | Soucy | A61L 27/3878 | |

OTHER PUBLICATIONS

Stachel et al., Biomacromolecules 2010, 11, 698-705 (Year: 2010).*
Fuchs et al., J. Microencapsulation, 2010; 27(8): 747-754 (Year: 2010).*
Nichol et al., Biomaterials 31 (2010) 5536-5544 (Year: 2010).*
Kuwahara et al., Tissue Engineering: Part C, vol. 16, No. 4, 2010 (Year: 2010).*
Ou et al., Nature Communications (2023) 14:322 (Year: 2023).*
Rajabi et al., Tissue Engineering: Part A, vol. 27, Nos. 11 and 12 (2021) (Year: 2021).*
Choi et al., Acta Biomaterialia 95 (2019) 285-296 (Year: 2019).*
Jaipan et al., MRS Communications (2017), 7, 416-426 (Year: 2017).*
Agren, M. S. et al., "Proliferation and Mitogenic Response to PDGF-BB of Fibroblasts Isolated from Chronic Venous Leg Ulcers is Ulcer-Age Dependent." (1999) J. Invest. Dermatol. 112 (4), 463-469.
Banyai, L. et al., "Structure and Domain-Domain Interactions of the Gelatin-binding Site of Human 72-Kilodalton Type IV Collagenase (Gelatinase A, Matrix Metalloproteinase 2)." (1996) J. Biol. Chem. 271 (20), 12003-12008.
Bonner, et al. "PDCF-Stimulated Fibroblast Proliferation Is Enhanced Synergistically by Receptor-Recogn ized a2,-acroglobulin." Journal of Cellular Physiology 145:I-8 (1990).
Burdick, J. A., et al., "Photoencapsulation of osteoblasts in injectable RGD-modified PEG hydrogels for bone tissue engineering." (2002) Biomaterials 23 (22), 4315-4323.
Chaudhuri, O., et al., "Hydrogels with tunable stress relaxation regulate stem cell fate and activity." (2016) Nat. Mater., 2016, 15, 326-334.
Deuel, T. F. et al., "Growth Factors and Wound Healing: Platelet-Derived Growth Factor as a Model Cytokine." (1991) Annu. Rev. Med. 1991, 42, 567-584.
DiMatteo, R., et al., "In situ forming injectable hydrogels for drug delivery and wound repair." (2018) Adv. Drug Deliv. Rev., 127, 167-184.
Dinh, T. N., et al., "Gelatin Hydrogel Combined with Polydopamine Coating to Enhance Tissue Integration of Medical Implants." (2018) ACS Biomater. Sci. Eng., 2018, 4, 3471-3477.
Griffin, D.R., et el., "Accelerated wound healing by injectable microporous gel scaffolds assembled from annealed building blocks." (2015) Nat. Mater. 14 (7), 737-744.
Groll, J. et al., "A novel star PEG-derived surface coating for specific cell adhesion." (2005) J. Biomed. Mater. Res., Part A, 74 (4), 607-617.
Hou, S. , et al., "Injectable Macroporous Hydrogel Formed by Enzymatic Cross-Linking of Gelatin Microgels." ACS Appl Bio Mater. Nov. 19, 2018; 1(5): 1430-1439.
Jeong, K. J., et al., "Interplay between Covalent and Physical Interactions within Environment Sensitive Hydrogels." Biomacromolecules 2009, 10, 5, 1090-1099.
Koh, J., et al., "Enhanced In Vivo Delivery of Stem Cells using Microporous Annealed Particle Scaffolds." (2019) Small, 15, 903147.
Li, et al., "Gelatin Microgel Incorporated Poly(ethylene glycol)-Based Bioadhesive with Enhanced Adhesive Property and Bioactivity." ACS Appl. Mater. Interfaces 2016, 8, 19, 11980-11989.
Li, J. et al., "Injectable and biodegradable hydrogels: gelation, biodegradation and biomedical applications." Chem. Soc. Rev., 2012, 41, 2193-2221.
Maddaus, A., et al., "Design and fabrication of bio-hybrid materials using inkjet printing." Biointerphases 11, 041002 (2016).
Jeong, K. J., et al., "Interplay between Covalent and Physical Interactions within Environment Sensitive Hydrogels." Biomacromolecules 2009, 10, 5, 1090-1099.
Koh, J., et al., "Enhanced In Vivo Delivery of Stem Cells using Microporous Annealed Particle Scaffolds." (2019) Small, 15, 903147.
Li, et al., "Gelatin Microgel Incorporated Poly(ethylene glycol)-Based Bioadhesive with Enhanced Adhesive Property and Bioactivity." ACS Appl. Mater. Interfaces 2016, 8, 19, 11980-11989.
Li, J. et al., "Injectable and biodegradable hydrogels: gelation, biodegradation and biomedical applications." Chem. Soc. Rev., 2012, 41, 2193-2221.
Maddaus, A., et al., "Design and fabrication of bio-hybrid materials using inkjet printing." Biointerphases 11, 041002 (2016).

(Continued)

*Primary Examiner* — Robert S Cabral

(74) *Attorney, Agent, or Firm* — Hamilton, Brook, Smith & Reynolds, P.C.

(57) ABSTRACT

Injectable macroporous hydrogels, and methods of producing same, are described. The injectable macroporous hydrogels may be formed by mixing gelatin microgels with an enzyme. In at least some embodiments, the enzyme may be transglutaminase, and more specifically microbial transglutaminase (mTG).

20 Claims, 23 Drawing Sheets

(56) References Cited

OTHER PUBLICATIONS

McBeath, R., et al., "Cell Shape, Cytoskeletal Tension, and RhoA Regulate Stem Cell Lineage Commitment." Developmental Cell, vol. 6, 483-495, Apr. 2004.
McDermott, M. K., et al., Mechanical Properties of Biomimetic Tissue Adhesive Based on the Microbial Transglutaminase-Catalyzed Crosslinking of Gelatin. Biomacromolecules 2004, 5, 4, 1270-1279.
Mladenovska, K., et al., "Biodegradation and drug release studies of BSA loaded gelatin microspheres." (2002) Int. J. Pharm. 242 (1-2), 247-249.
Munoz, Z., et al., "Gelatin hydrogels formed by orthogonal thiol-norbornene photochemistry for cell encapsulation." Biomaterials Science (2014), 28 pages.
Murphy, C. M., et al., "The effect of mean pore size on cell attachment, proliferation and migration in collagen glycosaminoglycan scaffolds for tissue engineering." (2010) Biomaterials 31 (3), 461-466.
Nguyen, AH. et al., "Gelatin Methacrylate Microspheres for Growth Factor Controlled Release." (2015) Acta Biomater. 13, 101-110.
Nicodemus, G.D., et al., "Cell Encapsulation in Biodegradable Hydrogels for Tissue Engineering Applications." (2008) Tissue Eng. Part B Rev., 14, 149-165.
Salvador-Culla, B., et al., "Titanium Coating of the Boston Keratoprosthesis." Translational Vision Science & Technology Apr. 2016, vol. 5, 17. p. 1-12.
Scott, G., et al., "The density of random close packing of spheres." (1969) Journal of Physics D: Applied Physics, vol. 2, No. 6.
Seliktar, D., "Designing Cell-Compatible Hydrogels for Biomedical Applications." Science Jun. 1, 2012: vol. 336, Issue 6085, pp. 1124-1128.
Shearier, E. R., et al., "In Vitro Cytotoxicity, Adhesion, and Proliferation of Human Vascular Cells Exposed to Zinc." ACS Biomater Sci Eng. Apr. 11, 2016; 2(4): 634-642.
Shin, S. R., et al., "Cell-laden Microengineered and Mechanically Tunable Hybrid Hydrogels of Gelatin and Graphene oxide." Adv Mater. Nov. 26, 2013; 25(44): 6385-6391.
Thrailkill, K. M. et al., "Physiological matrix metalloproteinase concentrations in serum during childhood and adolescence, using Luminex® Multiplex technology." Clin Chem Lab Med. 2005 ; 43(12): 1392-1399.
Truong, V. X., et al., "Simultaneous Orthogonal Dual-Click Approach to Tough, in-Situ-Forming Hydrogels for Cell Encapsulation." J. Am. Chem. Soc. 2015, 137, 4, 1618-1622.
Van Den Bulcke, A. I., et al., "Structural and Rheological Properties of Methacrylamide Modified Gelatin Hydrogels." Biomacromolecules 2000, 1, 31-38.
Wang, D. A., et al., "Multifunctional chondroitin sulphate for cartilage tissue-biomaterial integration." (2007) Nat. Mater., 6, 385-392 (p. 1-8).
Wang, L. et al., "Hydroxyapatite for Keratoprosthesis Biointegration." (2011) Invest. Ophthalmol. Visual Sci. 52 (10), 7392-7399.
Wang, M. 0., et al., "Evaluation of the In Vitro Cytotoxicity of Crosslinked Biomaterials." Biomacromolecules. May 13, 2013; 14(5): 1321-1329.
Weber, L. M. et al., "The effects of cell-matrix interactions on encapsulated B-cell function within hydrogels functionalized with matrix-derived adhesive peptides." Biomaterials vol. 28, Issue 19, Jul. 2007, pp. 3004-3011.
Yang, G. et al., "Assessment of the characteristics and biocompatibility of gelatin sponge scaffolds prepared by various crosslinking methods." Scientific Reports vol. 8, Article No. 1616 (Jan. 25, 2018) p. 1-13.
Yang, Y., et al., "Influence of Cell Spreading Area on the Osteogenic Commitment and Phenotype Maintenance of Mesenchymal Stem Cells." Scientific Reports vol. 9, Article No. 6891 (May 3, 2019) p. 1-11.
Zhu, M., Y. et al., "Gelatin methacryloyl and its hydrogels with an exceptional degree of controllability and batch-to-batch consistency." Scientific Reports vol. 9, Article No. 6863 (May 3, 2019) p. 1-13.

* cited by examiner

FIG. 2A
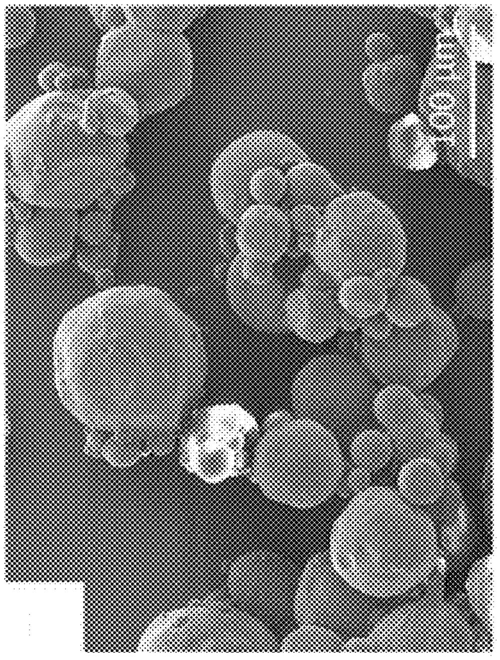
FIG. 2B
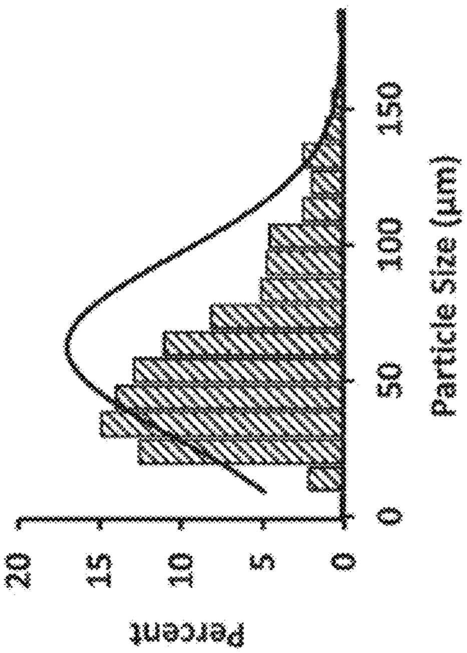
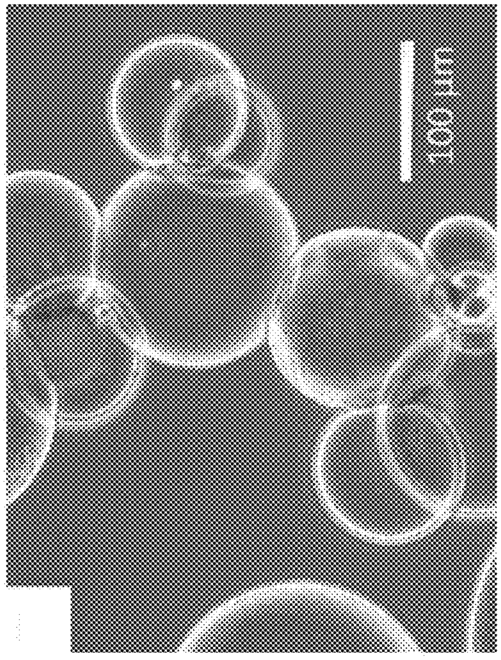
FIG. 2C
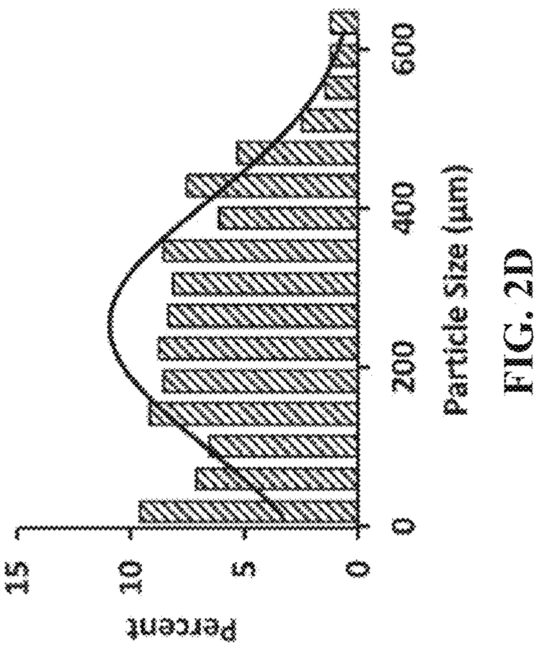
FIG. 2D

Actin Nuclei Composite

Porous hydrogel

Nonporous hydrogel

FIG. 8H
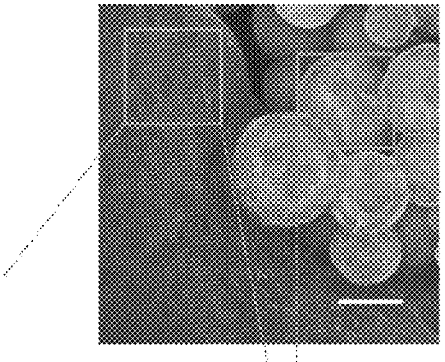
FIG. 8I
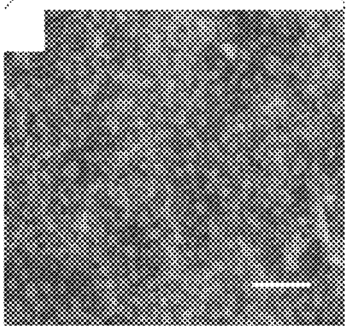
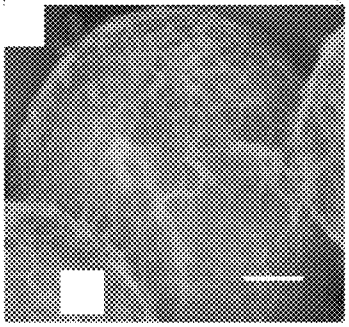
FIG. 8J
FIG. 9A
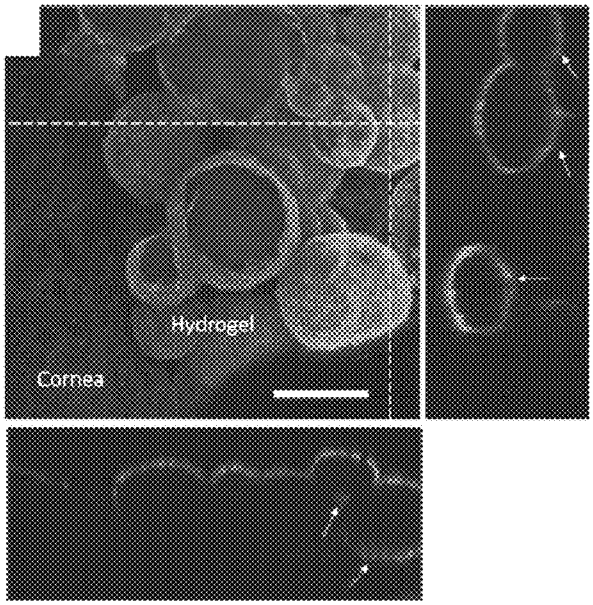
FIG. 9B
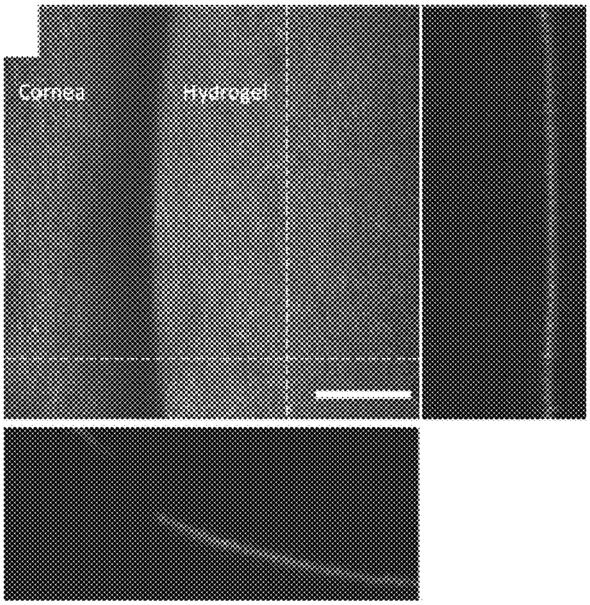

FIG. 17A
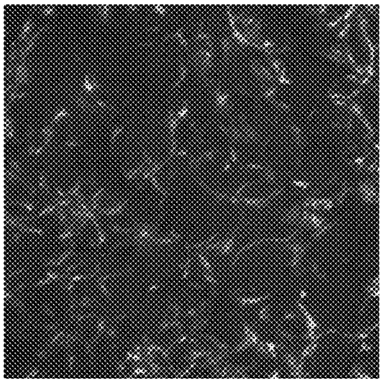
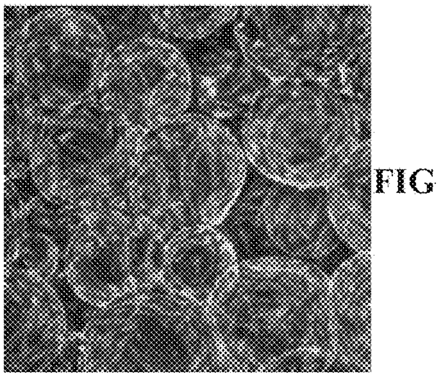
FIG. 17B
FIG. 17C
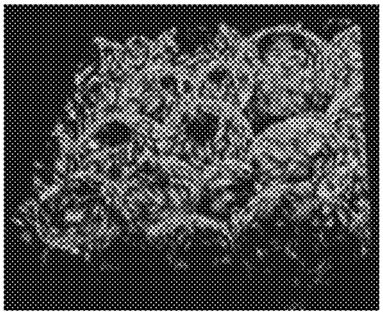
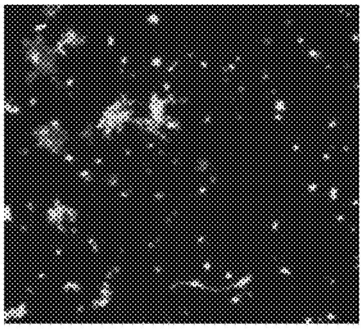
FIG. 17D
FIG. 18A
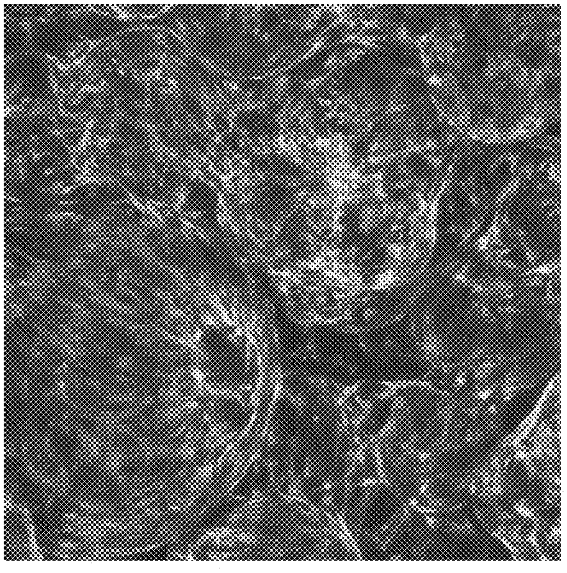
FIG. 18B
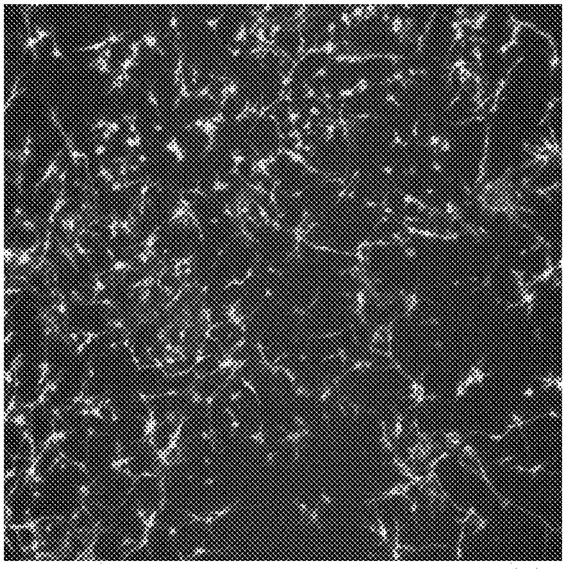

Modulus (Pa)

Modulus (Pa)

FIG. 32A FIG. 32B FIG. 32C
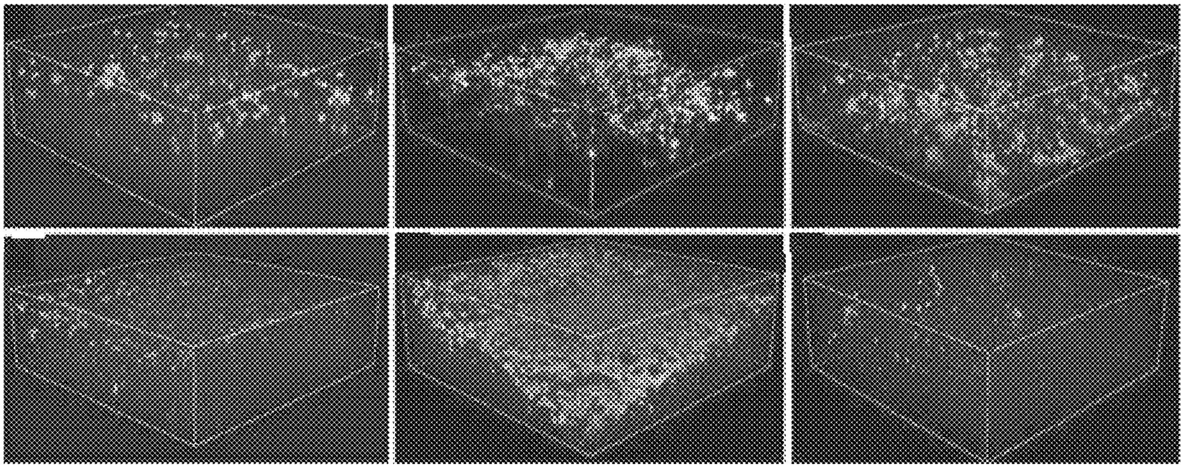
FIG. 32D FIG. 32E FIG. 32F
FIG. 33A
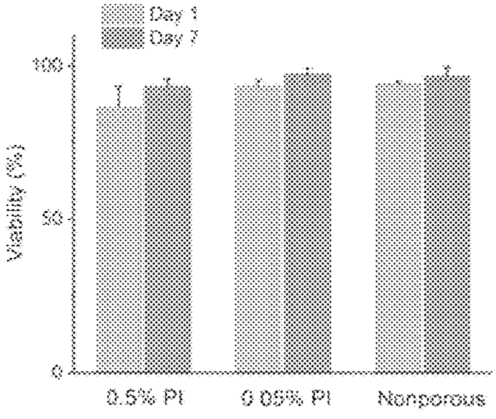
FIG. 33B
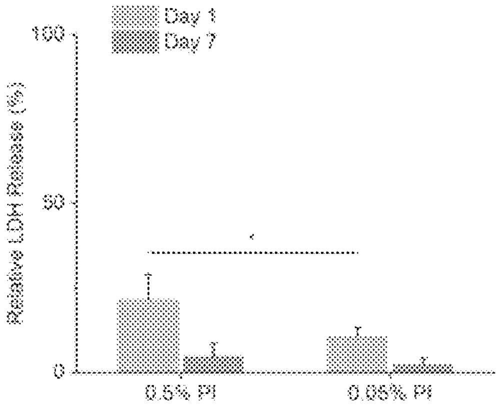

INJECTABLE POROUS HYDROGELS

RELATED APPLICATIONS

This application claims benefit under 35 U.S.C. § 119(e) of U.S. Provisional application Ser. No. 62/802,816 filed Feb. 8, 2019, the disclosure of which is incorporated by reference herein in its entirety.

GOVERNMENT SUPPORT

This invention was made with government support under grant number 5P20GM113131-03 awarded by the NIH. The government has certain rights in this invention.

FIELD OF THE INVENTION

Injectable macroporous hydrogels, and methods of producing same, are described. The macroporous hydrogels may be prepared in a manner that includes live cells and can be used to deliver live cells to tissues and subjects.

BACKGROUND OF THE INVENTION

Injectable hydrogels can be useful tools for facilitating wound healing because they conform to the irregular shapes of wounds, serving as a temporary matrix during the healing process. However, the lack of inherent pore structures of most injectable hydrogels prohibits desired interactions with the cells of the surrounding tissues, limiting their clinical efficacy.

SUMMARY OF THE INVENTION

In some aspects of the invention, a method for producing an injectable porous hydrogel is provided, the method including, preparing gelatin microgels; mixing the gelatin microgels with a cross-linking enzyme to produce the injectable porous hydrogel; and curing the injectable porous hydrogel. In certain embodiments, the cross-linking enzyme includes a transglutaminase and optionally includes a microbial transglutaminase (mTG). In certain embodiments, mixing the gelatin microgels with the transglutaminase includes: mixing the gelatin microgels with the cross-linking enzyme at a 5:1 ratio. In some embodiments, the mixture also includes phosphate-buffered saline (PBS). In some embodiments, curing the injectable porous hydrogel includes incubating the injectable porous hydrogel at about 37° C. In certain embodiments, curing the injectable porous hydrogel includes incubating the hydrogel at a predetermined temperature for at least 1 minutes, 5 minutes, 10 minutes, 20 minutes, 30 minutes, 40 minutes, 50 minutes, 60 minutes, 70 minutes, 80 minutes, 90 minutes, or more than 90 minutes. In some embodiments, curing the injectable porous hydrogel includes: mixing the gelatin microgels with a photoinitiator. In some embodiments, the photoinitiator includes at least one of Irgacure 2959, vitamin B12, and lithium phenyl-2,4,6-trimethylbenzoylphosphinate (LAP). In some embodiments, curing the injectable porous hydrogel includes: contacting the mixture that includes the gelatin microgels and the photoinitiator with ultraviolet (UV) light. In certain embodiments, the mixture that includes the gelatin microgels and the photoinitiator is contacted with the UV light for at least 5, 10, 20, 30, 40, 50, 60, 70, 80, 90, 100, 110, 120, 130, 140, 150, 160, 170, 180, 190, 200, 210, 220, 230, or 240 seconds. In some embodiments, the mixture that includes the gelatin microgels and the photoinitiator is contacted with the UV light for from 2-4 minutes. In certain embodiments, the method also includes including one or more live cells in the mixture that includes the gelatin microgels to produce a solution that includes one or more live cells and gelatin microgels; wherein the solution that includes the gelatin microgels and the one or more live cells is mixed with the cross-linking agent. In some embodiments, the one or more live cells include stem cells. In some embodiments, the stem cells includes one or more of: adipose stem cells, mesenchymal stem cells, hematopoietic stem cells, and embryonic stem cells. In certain embodiments, the one or more live cells includes one or more of: an endothelial cell, an epithelial cells, a neuronal cell, an umbilical vein endothelial cell (HUVEC), a vascular cell, a coronary artery endothelial cell, an aortic endothelial cell, a pulmonary artery endothelial cells, and a cardiomyocyte. In some embodiments, the live cells are vertebrate cells, optionally are mammalian cells, and optionally are human cells. In some embodiments, the gelatin microgels includes gelatin and methacrylated gelatin (GelMA). In some embodiments, the gelatin:GelMA mass ratio is 2:1. In certain embodiments, the concentration of the photoinitiator in the mixture comprising the microgels is 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1% (w/v). In some embodiments, the concentration of the photoinitiator in the mixture is between 0.005% and 0.05% (w/v).

According to another aspect of the invention, a composition comprising a microgel solution is provided, the solution including: microgels; a cross-linking enzyme; and a photoinitiator. In certain embodiments, the microgels includes gelatin and methacrylated gelatin (GelMA). In some embodiments, the cross-linking enzyme includes one or more of: a transglutaminase, genipin, factor XIIIa, and horse radish peroxidase (HRP). In some embodiments, the transglutaminase is a microbial transglutaminase. In some embodiments, the photoinitiator includes one or more of: Irgacure 2959, vitamin B12, and lithium phenyl-2,4,6-trimethylbenzoylphosphinate (LAP). In certain embodiments, the composition also includes phosphate buffered saline. In some embodiments, the composition also includes an antioxidant agent. In some embodiments, the antioxidant agent is ascorbic acid. In certain embodiments, the composition also includes one or more live cells. In some embodiments, the one or more live cells include stem cells. In some embodiments, the stem cells include one or more of: adipose stem cells, mesenchymal stem cells, hematopoietic stem cells, and embryonic stem cells. In some embodiments, the one or more live cells include one or more of: an endothelial cell, an epithelial cells, a neuronal cell, an umbilical vein endothelial cell (HUVEC), a vascular cell, a coronary artery endothelial cell, an aortic endothelial cell, a pulmonary artery endothelial cells, and a cardiomyocyte. In certain embodiments, the cells are vertebrate cells, optionally are mammalian cells, and optionally are human cells.

According to yet another aspect of the invention, a method of preparing a porous hydrogel is provided, the method including contacting any embodiment of an aforementioned composition with UV light for a time effective for the photoinitiator to activate cross-linking of the microgel solution.

According to another aspect of the invention, a method of delivering a live cell into a subject is provided, the method including: preparing any embodiment of an aforementioned composition, wherein the microgel solution includes one or more live cells, administering the composition to a subject; and cross-linking the microgel solution to form a porous hydrogel comprising the one or more live cells. In some embodiments, a means for the cross-linking includes contacting the microgel solution with UV light for a time effective for the photoinitiator-activated cross-linking of the microgel solution in the subject. In certain embodiments, the one or more live cells include stem cells. In some embodiments, the stem cells includes one or more of: adipose stem cells, mesenchymal stem cells, hematopoietic stem cells, and embryonic stem cells. In some embodiments, the one or more live cells include one or more of: an endothelial cell, an epithelial cells, a neuronal cell, an umbilical vein endothelial cell (HUVEC), a vascular cell, a coronary artery endothelial cell, an aortic endothelial cell, a pulmonary artery endothelial cells, and a cardiomyocyte. In some embodiments, the live cells are vertebrate cells, optionally are mammalian cells, and optionally are human cells.

According to another aspect of the invention, an injectable porous hydrogel that includes gelatin microgels cross-linked using transglutaminase, is provided. In certain embodiments, the transglutaminase is microbial transglutaminase (mTG). In some embodiments, the injectable porous hydrogel also includes a photoinitiator. In some embodiments, the photoinitiator includes at least one of Irgacure 2959, vitamin B12, and lithium phenyl-2,4,6-trimethylbenzoylphosphinate (LAP). In certain embodiments, the injectable porous hydrogel also includes one or more live cells. In some embodiments, the one or more live cells include stem cells. In some embodiments, the stem cells include one or more of: adipose stem cells, mesenchymal stem cells, hematopoietic stem cells, and embryonic stem cells. In some embodiments, the one or more live cells include one or more of: an endothelial cell, an epithelial cells, a neuronal cell, an umbilical vein endothelial cell (HUVEC), a vascular cell, a coronary artery endothelial cell, an aortic endothelial cell, a pulmonary artery endothelial cells, and a cardiomyocyte. In certain embodiments, the live cells are vertebrate cells, optionally are mammalian cells, and optionally are human cells. In some embodiments, the gelatin microgels comprise gelatin and methacrylated gelatin (GelMA). In certain embodiments, the gelatin and the GelMA are present in a mass ratio of 2:1.

BRIEF DESCRIPTION OF THE DRAWINGS

For a more complete understanding of the present disclosure, reference is now made to the following description taken in conjunction with the accompanying drawings.

FIG. 2A-F provides photomicrographs, graphs, and a photo illustrating certain aspects of gelatin microgels. FIG. 2A is a scanning electron microscope (SEM) image of lyophilized microgels. FIG. 2B is a graph showing size distribution of the lyophilized microgels of FIG. 2A. FIG. 2C is an optical microscope image of gelatin microgels after swelling in phosphate-buffered saline (PBS). FIG. 2D is a graph showing size distribution of the microgels after swelling in PBS of FIG. 2C. FIG. 2E is a photograph showing a porous gelatin hydrogel, including fluorescein for enhance visualization, extruded through a 26 gauge needle. FIG. 2F is a microscope image, with a scale bar of 400 μm, of gelatin microgels after extrusion from the 26 gauge needle of FIG. 2E.

FIG. 3A is an optical microscope image of a porous gelatin hydrogel, formed by mixing gelatin microgels with microbial transglutaminase (mTG). Scale bar equals 200 μm. FIG. 3B is a SEM image of porous hydrogel after critical point drying. 500 μm. FIG. 3C is a 3-dimensional rendition of confocal microscope images of the porous hydrogel of FIG. 3B.

FIG. 4A is a graph showing a time sweep rheological characterization of hydrogels. Top trace shows result for gelatin microgels+mTG (=macroporous hydrogel). Middle trace shows results from gelatin solution+mTG (nonporous hydrogel). The lower trace shows results from gelatin microgels. FIG. 4B is a temperature sweep rheological characterization of hydrogels. Uppermost trace at the start shows result from gelatin solution+mTG (nonporous hydrogel), the middle trace at the start shows results from gelatin microgels+mTG (=macroporous hydrogel). Lower most trace shows results from gelatin microgels. FIG. 4C is a bar graph illustrating time, frequency, and temperature sweep rheological characterizations for porous hydrogel, nonporous hydrogel, and microgel.

FIG. 6A is a bar graph showing human dermal fibroblast (hDF) proliferation on hydrogels. Proliferation measured by the alamarBlue assay was normalized to the proliferation on tissue culture polystyrene (TCPA). The data are means and standard deviation (n=4, *$p<0.05$). FIG. 6B illustrates cell viability of hDFs on porous and nonporous hydrogels 14 days after initial seeding, in accordance with embodiments of the present disclosure. Viable cells were stained by calcein-AM, and dead cells were stained by ethidium homodimer-1. The scale bar is 200 μm.

FIG. 7A is a porous hydrogel. FIG. 7B is a nonporous hydrogel. The actin cytoskeleton of hDFs was stained with ActinRed555. The insets on the right and at the bottom of each of FIGS. 7A and B are the cross-sectional images correspond to the vertical and horizontal dotted lines, respectively. The white arrows in the insets indicate the cells that grew underneath the microgels through the interstitial space.

FIG. 8A-J provides photomicroscopic images demonstrating tissue adhesion of porous and nonporous gelatin hydrogels. FIG. 8A and FIG. 8B illustrates porous hydrogel and nonporous hydrogel, respectively that were injected into a hole in an excised porcine cornea and cultured for 14 days. The hydrogels stably adhered to the cornea tissues during that period. The cornea tissues turned opaque during the culture. FIG. 8C and FIG. 8D provide confocal microscope images of a cornea-porous hydrogel interface, and cornea-nonporous hydrogel interface, respectively, at day 0. FIG. 8E and FIG. 8F provide confocal microscope images of a cornea-porous hydrogel interface, and cornea-nonporous hydrogel interface, respectively, at day 14. In FIG. 8C-F the actin cytoskeleton was stained red using ActinRed 555.

Dotted lines indicate the cornea-hydrogel interface with the arrows indicating the direction from cornea to hydrogel. The scale bar for FIG. 8A-B is 5 mm and for FIG. 8C-F is 200 μm. FIG. 8G illustrates 3-dimensional images constructed from Z-sections taken by confocal microscopy. Actin cytoskeleton was stained red using actinRed555 and cell nuclei were stained using DAPI. Dotted lines in the images indicate the cornea-hydrogel interface with arrows pointing a direction from the cornea to the hydrogel. The scale bar is 200 μm. FIG. 8H illustrates a maximum intensity projection of a confocal microscope image at a cornea-hydrogel interface of a porous hydrogel. The scale bar is 200 μm. FIG. 8I illustrates a high resolution image of a selected area of FIG. 8H, demonstrating specificity of actin staining. The scale bar is 50 μm. FIG. 8J illustrates a high resolution image of a selected area of FIG. 8H, demonstrating specificity of actin staining. The scale bar is 50 μm.

FIG. 9A-B provides photomicroscopic images showing cornea-hydrogel interfaces. Maximum intensity projections of confocal microscope images at a cornea-hydrogel interface for porous hydrogel (FIG. 9A) and nonporous hydrogel (FIG. 9B) on day 14 are shown. Actin cytoskeleton was stained red using actinRed555. Insets on the right and at the bottom are the cross-sections along the vertical and horizontal dotted lines, respectively. White arrows in the insets indicate cells that grew underneath microgels through interstitial space. The scale bar is 200 μm.

FIG. 11A shows FITC-BSA-loaded gelatin microgels. FIG. 11B is a confocal microscope image of a FITC-BSA-loaded gelatin microgel of FIG. 11A. FIG. 11C illustrates fluorescence intensity along the lateral line in FIG. 11B.

FIG. 13A is a schematic of hDF proliferation with the controlled release of PDGF experimental design for porous hydrogels (top container in diagram) and for non-porous hydrogels (bottom container in diagram). FIG. 13B is a bar graph showing relative proliferation of hDF cells in experiments using porous and nonporous hydrogels at day 14.

FIG. 15A shows results of study in which gelatin microgels, mixed with mTG, were injected into an 8 mm hole in a porcine cornea. FIG. 15B shows results of study in which gelatin/GelMA microgels were injected into an 8 mm hole in a porcine cornea without UV irradiation. FIG. 15C shows results of study in which gelatin/GelMA microgels were injected into an 8 mm hole in a porcine cornea, after the microgels were UV irradiated for about 2 minutes. FIG. 15D shows results of study in which gelatin/GelMA microgels were mixed with mTG, injected into an 8 mm hole in a porcine cornea, after the microgels mixed with mTG were UV irradiated for about 2 minutes.

FIG. 17A-D provides photomicroscopic images of hDFs under different experimental conditions. FIG. 17A illustrates a 2-dimensional projection of stacked confocal images of hDF encapsulation in a macroporous hydrogel, assembled using mTG, 1 day after encapsulation. FIG. 17B illustrates a 2-dimensional projection of stacked confocal images of hDF encapsulation in a macroporous hydrogel, assembled using mTB, 4 days after encapsulation. FIG. 17C illustrates a 3-dimensional rendition of the hDF encapsulation of FIG. 17B. FIG. 17D illustrates a 2-dimensional projection of stacked confocal images of hDF encapsulation in nonporous gelatin hydrogel, assembled by mixing gelatin solution with mTG in the presence of hDFs, 4 days after encapsulation, in accordance with embodiments of the present disclosure. In FIG. 17A-D, green and red fluorescence are from live and dead cells, respectively.

FIG. 18A-B provides photomicroscopic images of hDFs under different experimental conditions. FIG. 18A shows a 2-dimensional projection of 3-dimensional confocal microscope images of porous hydrogel including human adipose stem cells. FIG. 18B is a 2-dimensional projection of 3-dimensional confocal microscope images of nonporous hydrogel including human adipose stem cells. In the experiments, the human adipose stem cells were stained with live/dead assay. Prior to imaging, the human adipose stem cells were encapsulated in porous (FIG. 18A) or nonporous (FIG. 18B) hydrogel, cultured for one week in a growth media, followed by two weeks' culture in osteogenic differentiation media.

FIG. 19A shows the adipose stem cells cultured in the porous hydrogel differentiated into osteoblasts and deposited calcium minerals. FIG. 19B shows the adipose stem cells cultured in the nonporous hydrogel did not show evidence of osteoblast differentiation. The scale bar for FIG. 19A-B is 3 mm.

FIG. 23A shows nuclei staining, FIG. 23B shows Cx 43 staining, FIG. 23C shows actin staining, and FIG. 23D is a composite image.

FIG. 24A shows nuclei staining, FIG. 24B shows Cx 43 staining, FIG. 24C shows actin staining, and FIG. 24D is a composite image.

FIG. 25A is a schematic of dual-cross-linking of gelatin/GelMA microgels to form a bulk hydrogel. FIG. 25B is a scanning electron microscope (SEM) image of dry gelatin/GelMA microspheres. Scale bar=200 μm. FIG. 25C is a graph showing size distribution of dry microspheres. The average diameter=61±60 μm.

FIG. 25D is an optical micrograph of swelled gelatin/GelMA microgels. Scale bar=200 μm. FIG. 25E is a graph showing size distribution of swelled microgels. The average diameter=139±90 μm.

FIG. 31-F shows 2D projections of confocal microscope images of live/dead assay. FIG. 31A-C show results from Day 1 post encapsulation, FIG. 31D-F show results from Day 7 post encapsulation. The microgels were cured with mTG and UV irradiation using 0.5% (FIGS. 31A & D) or 0.05% (FIGS. 31B &E) PI concentration. Nonporous hydrogel was formed with mTG and UV irradiation using 0.05% PI concentration. Scale bar=100 μm.

FIG. 33A-B provides bar graphs illustrating viability and relative LDH release of encapsulated cells. FIG. 33A shows results when viability was measured through analysis of confocal microscopy images taken on day 1 and 7 post encapsulation (n=3). FIG. 33B shows results of relative LDH release measured through comparison to maximum LDH 2D culture controls, and acellular hydrogel negative controls (n=4).

DETAILED DESCRIPTION

Various embodiments of the present disclosure relate to cost-effective, highly biofunctional injectable macroporous hydrogels made of gelatin microgels cross-linked by an enzyme. The hydrogels exhibit pores large enough for cell migration. Viscoelastic properties of porous hydrogels disclosed herein are similar to those of a nonporous hydrogels produced by adding an enzyme to a homogeneous gelatin solution. The porous hydrogels support a higher cellular proliferation of human dermal fibroblasts (hDFs) than the nonporous hydrogels and allow migration of hDFs into the pores. Conversely, the hDFs were unable to permeate the surface of the nonporous hydrogels. To demonstrate potential use in wound healing, gelatin microgels were injected with enzyme into a cut out section of an excised porcine cornea. Due to the action of the enzyme, the porous hydrogel stably adhered to the cornea tissue. Confocal images demonstrate a significant number of cells from the cornea tissue migrated into the interstitial space of the porous hydrogel. The porous hydrogel was also used for the controlled release of platelet-derived growth factor (PDGF), increasing the proliferation of hDFs compared to the nonporous hydrogel. The gelatin microgel-based porous hydrogels of the present disclosure are thus useful for wound healing and tissue engineering. Methods of the invention can be used to prepare porous hydrogels comprising microgels un-modified gelatin and gelatin chemically modified with methacrylate group. Gelatin Methacryloyl (GelMA) is a non-limiting example of a gelatin chemically modified with a methacrylate that may be used in certain embodiments of methods and compositions of the invention.

Preparing Microgels

Gelatin is a heterogeneous mixture of water-soluble proteins of generally high average molecular weights. Generally, these proteins may be extracted by boiling skin, tendons, ligaments, bones, etc. Gelatin may be derived from fish sources, porcine sources, or beef sources, for example. While embodiments of the present disclosure may describe use of particular gelatin, one skilled in the art will appreciate that the present disclosure is not limited thereto, and that various other types of gelatin may be used.

Figure 1:
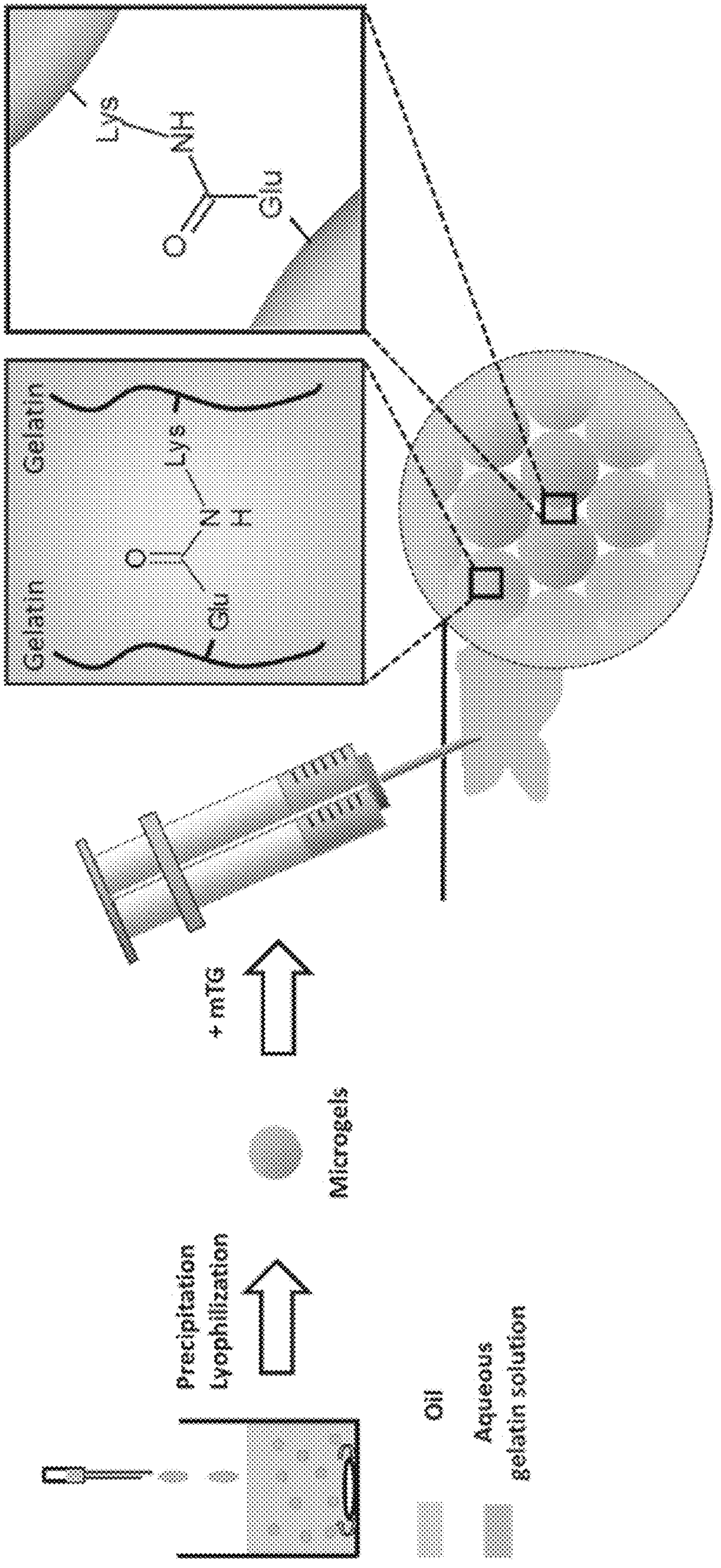
FIG. 1 is a schematic diagram illustrating microgel synthesis and formation of a porous hydrogel, in accordance with embodiments of the present disclosure. The diagram shows cross-linking gelatin microgels with mTG. mTG cross-links gelatins within the microgels and between microgels by creating amide bonds between glutamine (Glu) and lysine (Lys) residues.

FIG. 1 illustrates an example microgel synthesis and porous hydrogel formation scheme. According to at least some embodiments, a water-in-oil emulsion technique may be used to create gelatin microgels. The term "gelatin microgels" may be used interchangeably herein the term "microgels". In some embodiments of the invention, a gelatin microgel comprises gelatin and gelatin methacryloyl (GelMA). To prepare a plurality of microgels of the invention, gelatin may be dissolved in water or other aqueous liquid to produce an aqueous gelatin solution. The aqueous gelatin solution comprises a plurality of microgels, which may also be referred to herein as "microgel particles." In some embodiments of the invention, microgel particles produced using a synthesis method of the invention have an average size between 130 and 250 μm in diameter. In some embodiments of the invention a microgel particle has a diameter of at least 100, 110, 120, 130, 140, 150, 160, 170, 180, 190, 200, 210, 220, 230, 240, 250, or 260 μm. In some embodiments of the invention, a synthetic run to produce microgels, may yield a plurality of microgels having an average size of about 250 μm in diameter.

Following preparation, an aqueous gelatin solution may be added to an oil and stirred. A non-limiting list of oils and other hydrophobic materials that may be used include olive oil, acetone, chloroform, uncross-linked polydimethylsiloxane (PDMS), and chemical equivalents thereof. Various oils and other hydrophobic materials are envisioned as useful to add to an aqueous gelatin solution prepared as described in the present disclosure.

According to various embodiments of the invention, after stirring the aqueous gelatin solution in the oil, gelatin microgels may be precipitated out of solution. In some embodiments of the invention, a means for microgel precipitation comprises mixing the solution comprising the microgels with a precipitating agent such as, but not limited to acetone and an alcohol. Those in the art will recognize additional precipitating agents that are suitable for use in conjunction with methods disclosed herein to precipitate prepared microgels.

In some embodiments of the invention, gelatin microgels may be precipitated by mixing the microgel solution with a pre-cooled precipitating agent, for example pre-cooled acetone. A pre-cooled precipitating agent may be at a temperature below that of the microgel solution, which in some embodiments of the invention is at room temperature. Non-limiting examples of temperatures to which a precipitating agent may be cooled and used in a method of the invention is: 2, 3, 4, 5, 6, 7, 8, 9, 10, 11, 12, 13, 14, 15, 16, 17, 18, 19, 20, 21, 22, or 23 degrees C., including all temperatures within the listed range of temperatures. In some embodiments of the invention, the mixture comprising the precipitating agent and the microgel solution is held in a water-bath for an incubation period. The length of time for incubation period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 minutes in length, including all times within the range of listed times. In some embodiments the incubation time is greater than 35 minutes. In some embodiments of the invention, the incubation period comprises stirring or shaking of the mixture for all or a portion of the incubation time period.

Following the incubation of the mixture of the microgel solution and a precipitating agent, the microgels are separated from the oil and precipitating agent. Non-limiting means of separating prepared microgels from the oil and precipitating agent are vacuum filtration and centrifugation. Those in the art will recognize additional separation means suitable for use in conjunction with methods disclosed herein to separate microgels from oil and a precipitating agent. Following the separation the microgels are washed 1, 2, or more times with a precooled precipitating agent. In some embodiments of methods of the invention the washed microgels are lyophilized and then used or they may be lyophilized and frozen for later use. The microgels may be kept dry until used.

For use in an embodiment of a composition or method of the invention, microgels may be in solution with a water-based salt solution, such as but not limited to phosphate buffered saline (PBS). In some embodiments of the invention, a microgel solution comprises one or more of: a photoinitiator, a cross-linking enzyme, an antioxidant agent, gelatin, and GelMA.

Microgels, Hydrogels, and Cells

Gelatin microgels may, in at least some embodiments of the invention, be mixed with cells. A non-limiting list of cells that may be mixed with microgels of the invention includes stem cells, adipose cells, muscle cells, neuronal cells, epithelial cells, vertebrate endothelial cells, and cardiomyocytes. Stem cells may include adipose stem cells, mesenchymal stem cells, hematopoietic stem cells, and/or embryonic stem cells in at least some embodiments of the invention. Vertebrate endothelial cells may include mammal endothelial cells in at least some embodiments. The mammal endothelial cells may include human endothelial cells in at least some embodiments. The human endothelial cells may include human umbilical vein endothelial cells (HUVECs) coronary artery endothelial cells, aortic endothelial cells, and/or pulmonary artery endothelial cells, in at least some embodiments. Other types of cells may also be used in embodiments of the invention.

A mixture of gelatin microgels and cells may be cross-linked using techniques and materials described herein. As the gelatin microgels are cured, the cells may become encapsulated with the interstitial space. Unlike a "normal" case of cell encapsulation in nonporous hydrogels, the cells in a gelatin microgel of the invention is capable of spreading through the microgel and can proliferate rapidly because the cells are not trapped in a polymer mesh. Gelating microgels of the invention can be used to encapsulate living cells with the encapsulated cells remaining capable of growth and proliferation through the microgel.

Cross-Linking General Overview

In some embodiments of the invention a gelatin microgel (without cells or with cells mixed therewith) may be cross-linked. In certain methods of the invention, gelatins are cross-linked by creating amide bonds between glutamine (Glu) and lysine (Lys) residues of gelatin that comprises the microgels. In some embodiments of the invention, a means for cross-linking comprises contacting a microgel of the invention with an enzyme configured to, and capable of forming an isopeptide bond between a carboxamide group of a glutamine residue side chain and an amino group of a lysine residue side chain. Cross-linking of the gelatin microgels creates pores in the interstitial space among the microgels, and resulting pores that display sufficient size to permit for cell migration through the pores. The term "porous hydrogel" is used herein and denotes a hydrogel of the invention comprising pores in the interstitial spaces among the microgels used to prepare the hydrogel. A porous hydrogel of the invention may be prepared by cross-linking microgels in a manner that results in a hydrogel comprising pores in its microgel interstitial space. As used herein the term, "nonporous hydrogel" denotes a hydrogel that lacks the porosity of a porous hydrogel of the invention. The terms: "porous" and "macroporous" may be used interchangeably herein to describe a porous hydrogel of the invention. The terms "curing" and "cured" may be used interchangeably with the terms "cross-linking" and "cross-linked." Embodiments of methods of the invention may comprise one or both of enzymatic cross-linking and photoinitiated cross-linking.

Enzymatic Cross-Linking

Certain embodiments of methods of the invention comprise enzymatic cross-linking microgels. Non-limiting examples of enzymes capable of cross-linking gelatin microgels in methods and compositions of the invention are: transglutaminase, genipin, factor XIIIa, horse radish peroxidase (HRP), or a combination thereof. In at least some embodiments of the invention, the transglutaminase is a microbial transglutaminase. A transglutaminase used in a method of the invention may create covalent isopeptide bonds (cross-links) between peptide-bound glutamine and lysine residues. Other art-known cross-linking enzymes may be suitable for use in a method or composition of the invention. Cross-linking microgels of the invention results in a porous hydrogel. The porous hydrogel may be cured using various methods. In a non-limiting example, a porous hydrogel may be allowed to cure "on its own," without intervention. This type of curing may take place over about 30 minutes, according to at least some embodiments.

Photoinitiated Cross-Linking

Certain embodiments of methods of the invention comprise photoinitiated cross-linking microgels. A non-limiting example of photoinitiated cross-linking includes cross-linking a microgel solution and forming a porous hydrogel by contacting the microgel solution comprising a photoinitiator with ultraviolet (UV) light for a period of time sufficient to cross-link microgels in the solution. Certain embodiments of methods of the invention comprise UV curing to produce a porous hydrogel. Methods of the invention comprising UV curing may be performed using microgels of gelatin that are chemically modified with methacrylate group (GelMA). In certain embodiments of the invention, a porous hydrogel may be prepared from an injectable solution comprising gelatin microgels made of 2 parts gelatin and 1 part GelMA. One or more photoinitiators (PIs) may be incorporated within a GelMA-containing microgel solution of the invention. Photoinitiators that may be used include, but are not limited to, Irgacure 2959, vitamin B12, and lithium phenyl-2,4,6-trimethylbenzoylphosphinate (LAP).

As used herein the length of time of UV contact with a microgel solution of the invention may be referred to as the photoinitiated "curing time" of the microgel solution. In certain embodiments of the invention, a microgel solution comprises a photoinitiator (PI) and contact with UV light cures microgel solution resulting in a porous hydrogel. Photo-curing methods of the invention, such as UV curing, may result in faster curing than curing without intervention. For example, the length of time for curing with UV exposure may be at least 1, 2, 3, 4, 5, 6, 7, 8, 9, or 10 minutes. In some embodiments of the invention, the UV curing is performed over a time period of 2, 3, 4, or 5 minutes. In a non-limiting example, a solution comprising microgels and a 0.05% (w/v) concentration of a photoinitiator is cured with about 2-3 minutes contact with UV light.

It will be understood that the curing time for a microgel solution comprising a PI at a particular concentration will be longer than the curing time for the same microgel solution prepared with a higher concentration of the PI. Increasing the concentration of a PI in a microgel solution may reduce the length of curing time, but because PIs can generate free radicals, increasing the PI concentration may increase cytotoxic effects of the PI in a microgel solution. In certain embodiments of the invention in which a microgel solution comprises live cells, a PI concentration in the microgel solution may be between 0.005% and 0.06% (w/v), and the concentration may be selected, at least in part, to minimize potential cytotoxic effects of the PI on the cells. In some embodiments of the invention, the concentration of a PI in a microgel solution is at least: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1% (w/v). Different PIs may result in different levels of cytotoxicity and a PI with a lower risk of causing cytotoxicity may be used in methods and compositions of the invention. For example, though not intended to be limiting, the photoinitiator lithium phenyl-2,4,6-trimethylbenzoylphosphinate (LAP), may be included in a microgel solution of the invention due to one or more of: a lower cytotoxicity versus Irgacure 2959, the ability to include a relative higher concentration of the LAP for faster curing versus another PI, etc.

The presence of certain photoinitiators and UV light results in formation of free radicals, which result in a cytotoxicity. To reduce cytotoxicity resulting from a photoinitiator in a method of the invention, an antioxidant agent may be included in a microgel solution of the invention. An antioxidant agent may be a free radical scavenger, a non-limiting example of which is ascorbic acid. In some embodiments of the invention, a microgel solution comprising a photoinitiator also includes an antioxidant agent. In some embodiments of the invention, the antioxidant agent included in a microgel solution is ascorbic acid.

Certain embodiments of methods of the invention comprise both of enzymatic cross-linking and photoinitiated cross-linking. Mixing gelatin with a photoinitiators(s) allows for a dual cross-linking mechanism: (1) cross-linking of gelatin by an enzyme (e.g., transglutimase, etc.), which creates covalent bonds with surrounding tissues; and (2) cross-linking the photoinitiator(s) by UV irradiation, which causes rapid gelation. In at least some embodiments of the invention, UV irradiation may be applied during enzymatic cross-linking of a solution comprising cells and composite microgels, which include gelatin and GelMA. In some embodiments of the invention, a microgel solution comprises gelatin, GelMA, and a photoinitiator, and the microgel solution can be cross-linked using an enzymatic means and a photoinitiated means.

Gelatin/GelMA Microgels

Certain embodiments of microgels of the invention comprise a mixture of unmodified gelatin and GelMA. The ratio of gelatin:GelMA in a microgel solution of the invention may be from a 1:1 ratio through a 2:1 ratio by weight. In a non-limiting example gelatin/GelMA microgels of the invention are made from a 10% (w/v) aqueous mixture of unmodified gelatin and GelMA (80% substitution) at a 2:1 ratio by weight. A water-in-oil emulsion was created using this solution, which generated physically cross-linked polydisperse microspheres. Freeze-dried microgels prepared in this manner were spherical in shape with an average diameter of 61 (±60) μm. When equilibrated in an aqueous environment, the average diameter increased to 139 (±90) μm, which provides sufficient void space between assembled microgels (on the order of tens of microns in size) to result in adequate space for cell encapsulation.

It has now been determined that photo-curable microgels from a mixture of unmodified gelatin and GelMA have advantages over GelMA-only microgels, because the unmodified gelatin and GelMA microgels can be cured also by enzymatic cross-linking, and thermal stability of microgels can be fine-tuned by adjusting the gelatin/GelMA ratio. For example, the microgels that are made by GelMA only (80% substitution) are unstable at room temperature and the curing has to be done using chilled solutions,[18] which is not an ideal condition for in situ cell encapsulation. In comparison, microgels comprising gelatin and GelMA (2:1) are stable in an aqueous solution at room temperature, which permits their use to encapsulate cells under ambient conditions. Other gelatin/GelMA ratios can be used in methods of the invention. Those in the art will be able to use other ratios in conjunction with methods of the invention to prepare porous hydrogels for various uses, including, but not limited to: living cell encapsulation methods.

Gelatin/GelMA microgels can be cured to form a bulk hydrogel by photopolymerization in the presence of one or more photoinitiators (PIs) and the addition of mTG. Rapid curing of the gelatin/GelMA microgels and the stability of the resulting bulk hydrogel have been assessed (See Example 16 herein), and it has been determined that combinations of gelatin/GelMA microgels based porous hydrogels of the invention comprise sufficient physical cross-links among the gelatin chains, and enough covalent cross-links to remain stable and suitable for use in methods such as, but not limited to, living cell encapsulation. Embodiments of porous hydrogels of the invention may be prepared using dual-cross-linking by UV photopolymerization and mTG, which permits rapid curing of the gelatin/GelMA microgels with a low PI concentration.

The combination of gelatin and GelMA used to prepare porous hydrogels of the invention permits use of the resulting porous hydrogels in methods such as but not limited to cell encapsulation, with a less risk of toxicity and cell damage from exposure to PIs such as, but not limited to UV light, as compared to alternative hydrogels that require a higher level of the PI for cross-linking.

In some embodiments of the invention, UV irradiation may be used with a high PI concentration (a non-limiting example of which is 0.5%) resulting in rapidly increased G', and minimal changes after removal of the UV source. In some embodiments of methods of the invention, a combination of both curing methods (mTG+UV) resulted in a rapid increase of G' and a much stiffer hydrogel than a hydrogel cured by UV only, which can be attributed to the additional covalent cross-links formed by mTG. The effect of UV irradiation was much reduced when a low PI concentration (A non-limiting example of which is 0.05%) was used, and cross-linking by UV irradiation alone did not form a stable hydrogel. When both curing methods were combined (mTG+UV), microgels quickly formed a stable gel. Concentrations of PI and/or an amount/length of contact with a photopolymerizing agent such as UV light, can be adjusted to alter a characteristic of a porous hydrogel prepared using a method of the invention. In some embodiments of the invention a concentration of a PI in a microgel solution is from 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, up to 0.6% (w/v). In some embodiments of the invention, a PI concentration of greater than 0.06% (w/v) may be used, but may result in a concomitant increased risk of cytotoxicity.

Hydrogel Use

Porous hydrogels of the invention can be used for in situ cell encapsulation. In some embodiments, cell encapsulation using a porous hydrogel of the invention can be used to administer or deliver living cells to a subject. Delivery of living cells using methods and/or hydrogels of the invention can be used in wound healing therapy and in regenerative medicine.

In certain embodiments of the invention, microgels are prepared, mixed with living cells, and cross-linked to form a porous hydrogel comprising encapsulated living cells. The cells can be grown and can infiltrate through the porous hydrogel. In some embodiments of the invention, a microgel mixture comprising one or more types of living cells is delivered into a tissue and/or subject, and the microgels are cross-linked resulting in a porous hydrogel comprising the living cells positioned in or on the tissue and/or subject. In some embodiments of the invention, a microgel solution comprises gelatin and GelMA and the microgels are cross-linked by contacting the microgels with at least one enzyme capable of cross-linking gelatin microgels and by contacting the microgels with a photoinitiator, such as UV light. Each of the enzymatic cross-linking and the photopolymerizing cross-linking are performed in an amount suitable to produce a porous hydrogel for use in a living tissue and/or subject. The porous hydrogel comprising living cells can be delivered to a subject in the form of a "patch" or localized substrate that includes living cells that may continue to grow after delivery. The cells may assist in healing of a surgical incision, healing a wound, increasing cell growth in a region of tissue and/or in an organ, etc. Methods and hydrogels of the invention may also be used in organ and tissue culture, for example, by increasing cell growth, patching an opening, etc. In certain embodiments porous hydrogels of the invention are suitable to adhere to living tissues into which they are delivered.

Some embodiments of the invention comprise methods of using a porous hydrogel that is adhered to a tissue surface. In certain embodiments of the invention, adherence, which is also referred to herein as "adhesion," is between a porous hydrogel and a wet tissue surface. Certain independent factors contribute to stable adhesion of a hydrogel to tissue surface, including for example, a wet tissue surface. One factor is interfacial adhesion (i.e. cross-linking between the hydrogel and tissue) and another factor is cohesion (i.e. mechanical strength of the hydrogel). In certain embodiments of the invention, rapid and stable tissue adhesion of a microgel-based hydrogel of the invention results from simultaneous enhancement of both interfacial adhesion (by mTG) and cohesion (by UV)—which result from the dual-cross-linking approach of methods of the invention.

In a non-limiting example, successful use of a microgel-based injectable hydrogel for cell delivery has been shown using human dermal fibroblasts (hDFs). Unlike most hydrogel systems in which cells are homogeneously distributed in the hydrogel phase, cells are encapsulated in the interstitial space between microgels. In some embodiments of the invention, cell-encapsulating constructs are formed by curing microgels using both enzymatic means and UV irradiation. It has been determined that the cells encapsulated in the microporous hydrogels exhibited fully spread morphologies as early as day 1 post encapsulation. The rapid spreading of encapsulated cells, which is attributed to the presence of unrestricted void space within the porous hydrogels, is distinct from most nonporous hydrogels in which the encapsulated cells are trapped by the polymer chains and cannot spread immediately.

Cell spreading is an important phenomenon particularly in stem cell differentiation. For example, differentiation of stem cells may be enhanced with a larger cell spread area in various 2D cultures. Certain embodiments of microgel formulations of the invention, are injectable and induce rapid spreading of the encapsulated cells and thus are useful, for example, when differentiation of the encapsulated stem cells into a specific lineage (e.g. osteogenic) is desired. Another advantage of encapsulating cells in the pores of the microgel mixtures of the invention, is also illustrated by an observation that over time, sphericities of cells encapsulated using a microgel mixture of the invention decreased, as compared to a higher sphericity retained by cells encapsulated in a nonporous hydrogel.

Cells and Subjects

A cell used in methods of the invention may be a prokaryotic or a eukaryotic cell. Useful cells include but are not limited to mammalian cells. Examples of cells that can be included in methods and compositions of the invention include: neuronal cells, nervous system cells, cardiac cells, circulatory system cells, visual system cells, auditory system cells, secretory cells, endocrine cells, or muscle cells. In some embodiments, a cell used in conjunction with the invention may be a healthy normal cell, which is not known to have a disease, disorder or abnormal condition. In some embodiments, a cell used in conjunction with methods and channels of the invention may be an abnormal cell, for example, a cell that has been diagnosed as having a disorder, disease, or condition, including, but not limited to a degenerative cell, a neurological disease-bearing cell, a cell model of a disease or condition, an injured cell, etc. In some embodiments of the invention, a cell may be a control cell.

Methods of the invention may include use of cells obtained from culture, cells in solution, cells obtained from subjects, and/or cells in a subject (in vivo cells). Cells encapsulated in a porous hydrogel of the invention may be delivered to cultured cells, cultured tissues (e.g., brain slice preparations, etc.), and living subjects, etc. As used herein, a the term "subject" may refer to a human, non-human primate, cow, horse, pig, sheep, goat, dog, cat, rodent, fly or any other vertebrate or invertebrate organism.

EXAMPLES

Example 1

Microgel Synthesis and Cross-Linking

Gelatin microgel was prepared using the water-in-oil emulsion method described by Li et al. (2016) ACS Appl. Mater. Interfaces 8 (19), 11980-11989. Gelatin (type 1, from bovine and porcine bones) was dissolved in about 20 mL of deionized water at about 50° C. to about 55° C. to make an about 10% (w/v) solution. The gelatin solution was added dropwise to about 200 mL of olive oil at about 50° C. to about 55° C., and stirred for about 1 hour. The temperature of the mixture was lowered to reach room temperature (e.g., about 20° C. to about 25° C.) for about 30 minutes with stirring. Then, the mixture was placed in an ice-water bath for about 30 minutes with stirring to solidify the microgels by inducing physical cross-linking. Then, about 100 mL of pre-cooled acetone (at about 4° C.) was added into the mixture to precipitate the microgels with stirring for about 30 minutes in the ice-water bath. The microgels were separated from the olive oil and acetone through vacuum filtration and further washed twice with about 60 mL of pre-cooled acetone. The microgels were lyophilized and kept dry until use.

mTG at about 20% (w/v) concentration in phosphate-buffered saline (PBS) was mixed with about 10% (w/v) gelatin microgel in PBS at a 1:5 v/v ratio to form a porous hydrogel, or mixed with about 10% (w/v) gelatin solution in PBS at a 1:5 v/v ratio to form a nonporous hydrogel. The final concentration of mTG and gelatin was about 3.3% and about 8.3%, respectively.

Example 2

Characterization of Gelatin Microgels and Porous Hydrogel

The gelatin microgels were visualized with an optical microscope (EVOS XL, Life Technologies, Carlsbad, CA) and scanning electron microscope (SEM) (Tescan Lyra3 GMU FIB SEM, Bmo, Czech Republic). For SEM, the microgels were lyophilized and coated with gold/palladium to avoid charging. Size distribution of the gelatin microgels was obtained from the optical microscope and SEM images using ImageJ. After the porous hydrogel was formed, the detailed structure of the porous hydrogel was visualized with an optical microscope, SEM, and confocal microscope (Nikon AIR HD, Melville, NY). For the SEM imaging, the porous hydrogel was dried by critical point drying. For the confocal microscopy, the porous hydrogel was formed from the gelatin microgels mixed with fluorescein isothiocyanate-labeled bovine serum albumin (FTIC-BSA) (0.1%).

Figure 2E:
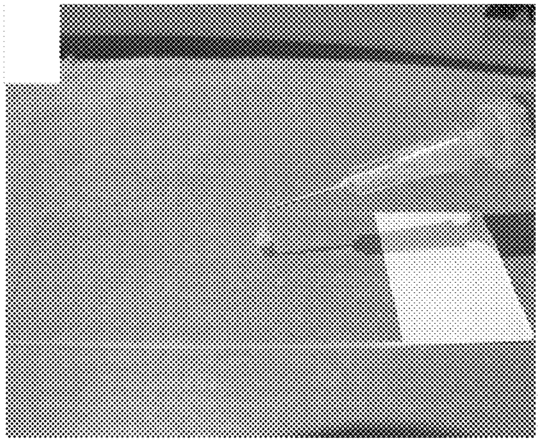
Figure 2F:
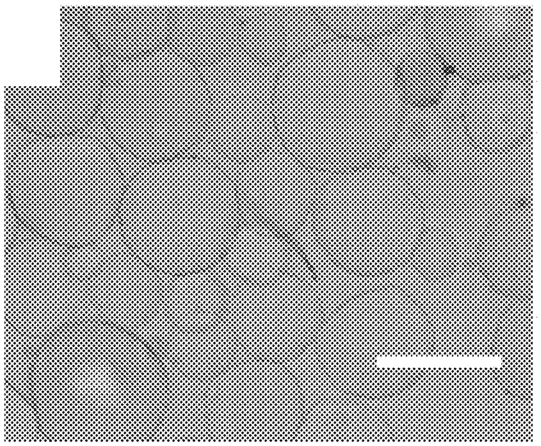

The gelatin microgels were spherical in shape (as illustrated in FIG. 2A) and polydispersed with an average diameter of about 63 μm (as illustrated in FIG. 2B). When the gelatin microgels were dispersed in water, they swelled significantly (as illustrated in FIG. 2C) to an average diameter of 253 μm (as illustrated in FIG. 2D). The swelling ratio was 14.7. At 10% (w/v) concentration and at about 37° C., gelatin microgels formed a viscous solution, making them injectable through a 26 gauge needle (as illustrated in FIG. 2E-F).

Figure 3A:
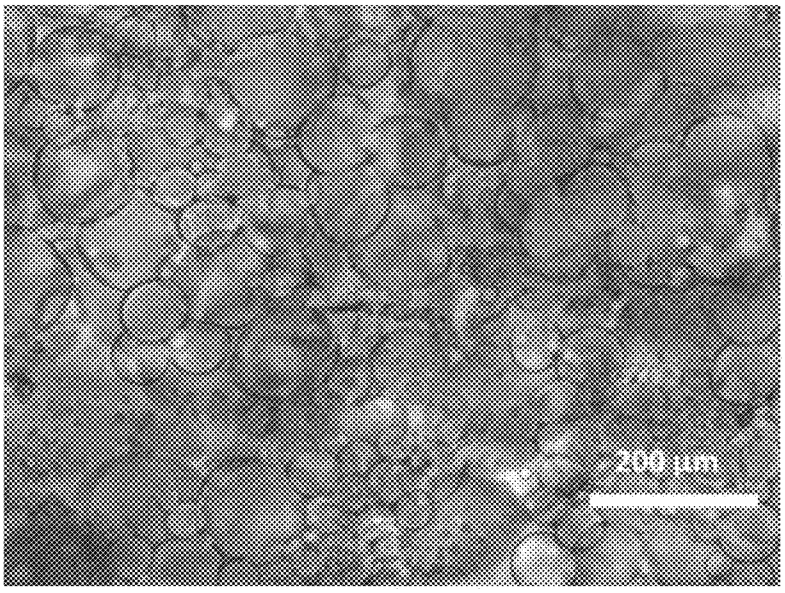
FIG. 3A-C provides photomicrographs of certain embodiments of hydrogels.
Figure 3B:
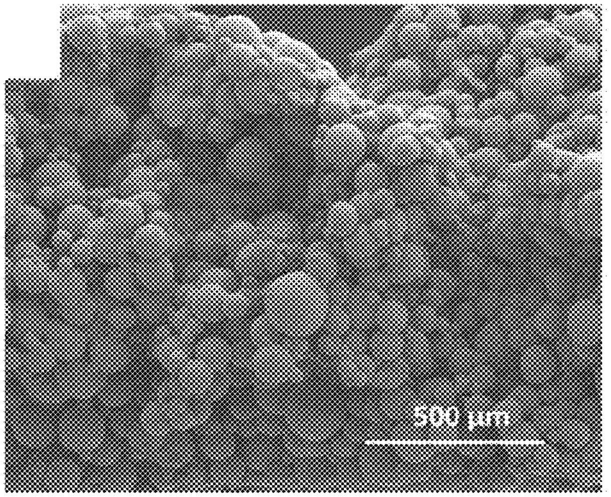
Figure 3C:
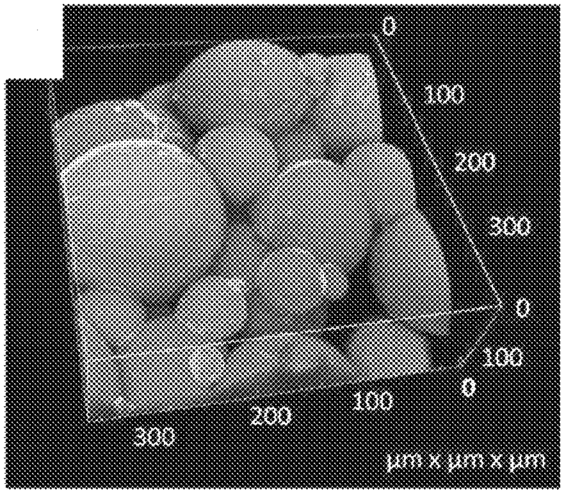

A bulk macroporous hydrogel was formed by annealing the gelatin microgels with mTG. When mixed with mTG, the microgel solution became more viscous over time (less than about 5 minutes) and eventually became a bulk gel. When viewed under the optical microscope, the assembly of spherical microgels within the hydrogel was evident (as illustrated in FIG. 3A). The SEM image demonstrates a three-dimensional network of spherical microgels with void space between microgels (as illustrated in FIG. 3B). Confocal microscope images of the hydrogel further confirmed these findings (as illustrated in FIG. 3C). The pore size was mostly in the range of tens of microns, which is large enough for cell migration. [Murphy, C. M. et al., (2010) Biomaterials 31 (3), 461-466]. The porosity of the hydrogel was estimated to be about 0.43 by the confocal microscope images. This value is in agreement with the void fraction of random packing of spheres, which is around about 0.4 for various sphere size distributions and materials [Scott, G. & Kilgour, D. (1969) J. Phys. D: Appl. Phys. 2 (6), 863].

Example 3

Rheological Characterization

The viscoelastic properties of porous hydrogel and nonporous hydrogels were characterized with a rheometer (TA Instruments AR 550, New Castle, DE). Either a gelatin microgel solution or plain gelatin solution was mixed with mTG and placed under a plane stainless steel geometry (diameter=2 cm). The linear viscoelastic regime was first determined by a stress sweep. The gelation kinetics was observed by a time sweep, with an oscillatory stress of 1 Pa at 10 rad/s and 37° C. Once the gelation was completed, a frequency sweep was performed between 0.1 rad/s and 100 rad/s with an oscillatory stress of 1 Pa at 37° C. For a temperature sweep, the temperature was changed from 4° C. to 45° C. with an oscillatory stress of 1 Pa at 10 rad/s.

Figure 4A:
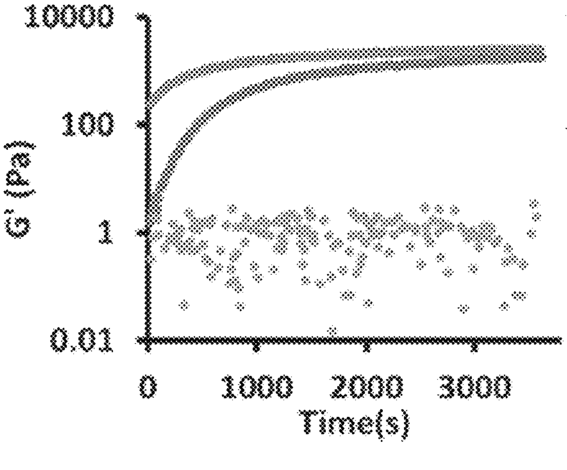
FIG. 4A-C provide graphs illustrating characteristics of certain embodiments of hydrogels of the invention.

Time-sweep measurements show the kinetics of the covalent cross-linking by mTG. Both G' and G" of the porous hydrogel (generated from mixing gelatin microgel with mTG) at t=0 were higher than the nonporous hydrogel (generated from mixing gelatin solution with mTG) because: (i) data collection for the porous hydrogel was more delayed than for the nonporous hydrogel (about 3 min) due to longer sample preparation time; and (ii) the gelatin concentration in the microgels was higher than that of the bulk gelatin solution because there was void space within the microgel solution even though its weight per volume concentration was the same (10%) as the bulk gelatin solution. In another study, the inclusion of gelatin microgels in a covalently cross-linked PEG hydrogel also resulted in a much higher initial G' and G" in a time sweep [Li, Y. et al., (2016) ACS Appl. Mater. Interfaces 8 (19), 11980-11989], although direct comparisons are difficult to be made due to the differences in the overall hydrogel structures. The final G' values after 1 hour were comparable to each other (as illustrated in FIG. 4A). G' of the gelatin microgels without mTG remained unchanged due to the lack of chemical cross-linking, indicating the gelatin microgels alone without cross-linking by mTG do not form a bulk hydrogel.

Figure 4B:
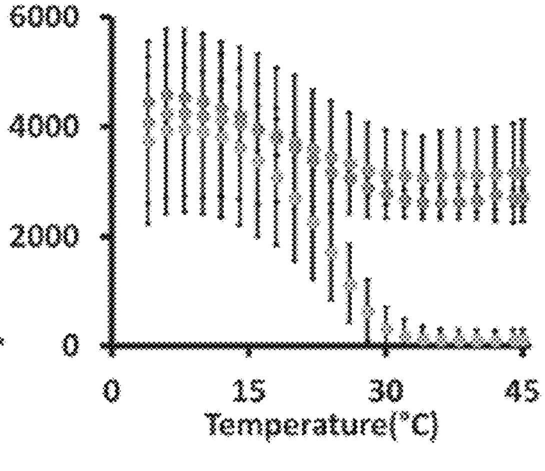
Figure 4C:
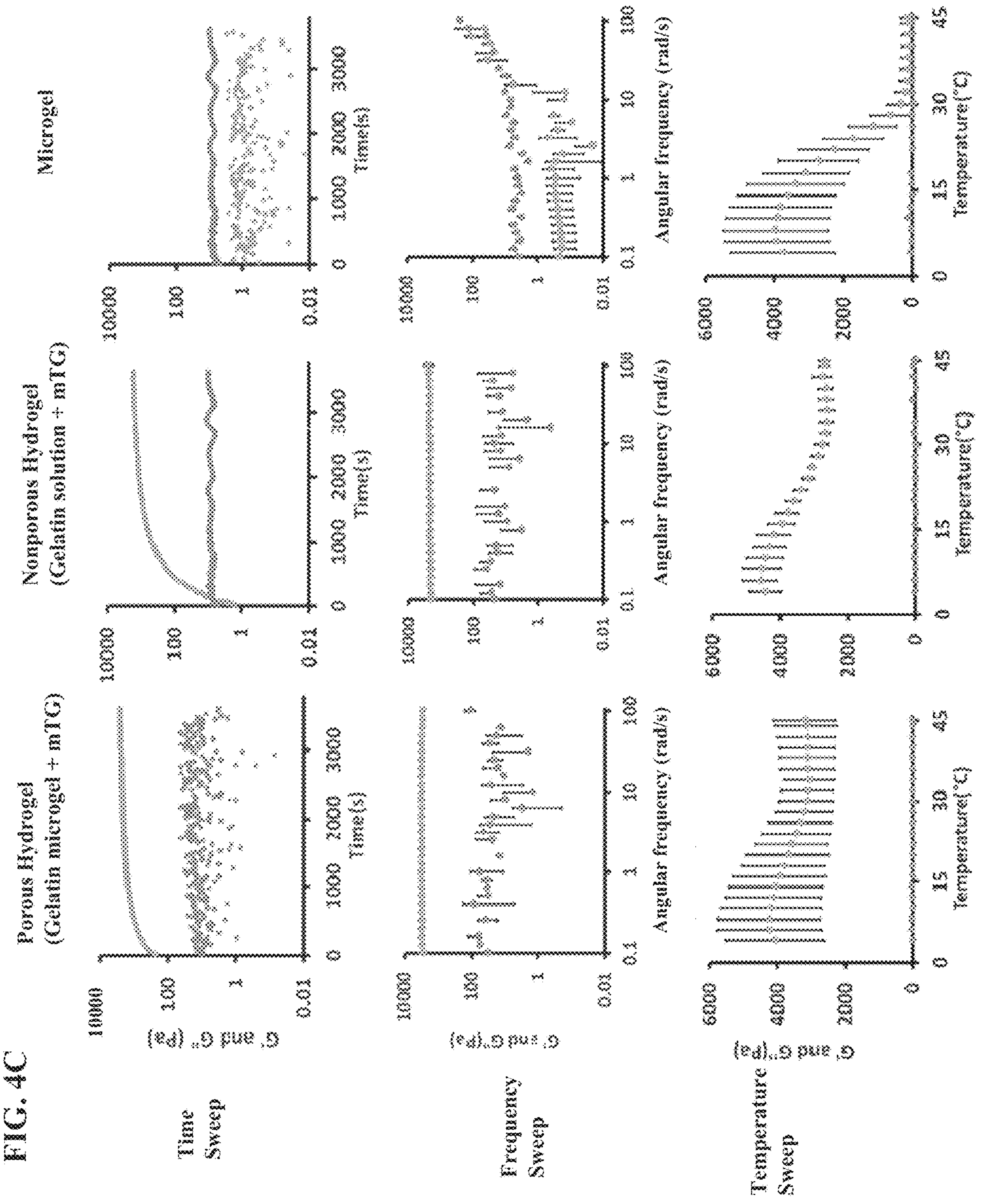

Once gelation was completed, G' was measured as a function of temperature (as illustrated in FIG. 4B). The temperature-sweep measurements provide more information about the nature of cross-links. As the temperature decreased, G' increased for both porous and nonporous hydrogels due to the formation of physical cross-links by hydrogen bonding. G' of gelatin microgels without mTG also increased for the same reason. As the temperature increased, the physical cross-links were weakened resulting in a continuous decrease in G' for both the porous and nonporous hydrogels. This trend continued until about 30° C., at which point G' reached a plateau at about 3000 Pa. This is attributed to the presence of the covalent bonds created by the actions of mTG because covalent cross-links by amide bonds in this temperature regime are stable. The fact that G' of the porous hydrogel is comparable to that of the nonporous hydrogel indicates that the chemical cross-linking by mTG occurred within the gelatin microgels as well as between microgels. In comparison, G' of microgels without mTG decreased until the gelatin microgels completely melted. A frequency sweep further confirmed that the viscoelastic properties of the porous hydrogel are similar to the nonporous hydrogel. The slight increase of G' as a function of frequency is a characteristic of the hydrogels that are cross-linked both physically and chemically [Jeong, K. J. & Panitch, A. (2009) Biomacromolecules 10 (5), 1090-1099]. FIG. 4C further illustrates time, frequency, and temperature sweep rheological characterizations for porous hydrogel, nonporous hydrogel, and microgel.

Example 4

Enzymatic Degradation of Hydrogels

The kinetics of the enzymatic degradation of porous and nonporous hydrogels was obtained by incubating the hydrogels in collagenase type II solution (concentration=0.5 U/mL) [Shin, S. R. et al., (2013) Adv. Mater. 25 (44), 6385-6391]. At different time points (0 hours, about 4 hours, and about 24 hours), the hydrogels were collected, lyophilized, and weighed to calculate the amount of degraded gelatin.

Figure 5:
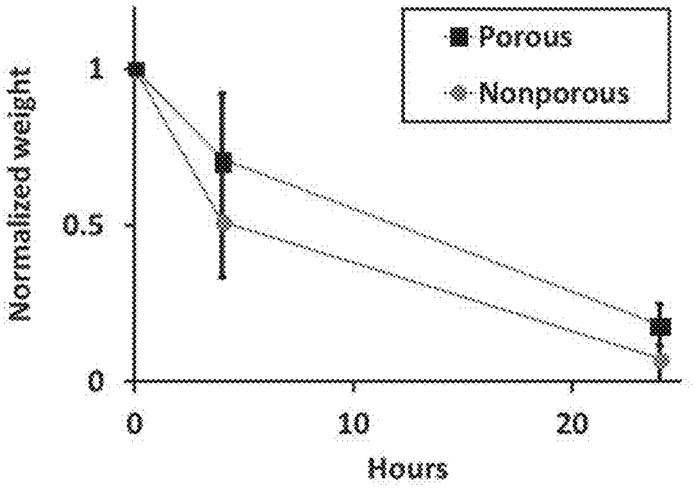
FIG. 5 is a graph illustrating degradation of porous and nonporous gelatin hydrogels by collagenase type II. Each hydrogel was lyophilized and weighed, and the values were normalized to the initial weight.

It is beneficial for a hydrogel added to a wound to be able to degrade over the course of the wound healing process. Gelatin can be degraded by many cell-secreted enzymes, such as collagenases and gelatinases [Banyai, L. et al., (1996) J. Biol. Chem. 271 (20), 12003-12008 and Mladenovska, K. et al, (2002) Int. J. Pharm. 242 (1-2), 247-249]. When incubated in collagenase type II solution, the porous hydrogel degraded slightly slower than the nonporous hydrogel (82% degradation for porous hydrogel vs 93% degradation for nonporous hydrogel at about 24 hours) (as illustrated in FIG. 5). However, there was no statistical significance of the difference ($p=0.198$ at about 4 hours and 0.086 at about 24 hours). This result indicates that the porous hydrogel can serve as a temporary matrix during the wound healing process.

Example 5

In Vitro Culture of Human Dermal Fibroblasts (hDFs) on Hydrogels

Human dermal fibroblasts (hDFs) were cultured in T75 flasks using Dulbecco's modified Eagle medium (DMEM) supplemented with 10% fetal bovine serum (FBS) and 1% penicillin/streptomycin (pen/strep). The culture was performed in a humidified chamber with 5% $CO_2$ at 37° C. Cells under passage 4 were used for all of the experiments. To test cellular proliferation on the hydrogels, the porous and nonporous hydrogels (about 600 μL) were formed in 24-well plates, followed by sterilization in 70% ethanol overnight. hDFs were seeded on the hydrogel surface with a seeding density of $1\times10^4$ cells/$cm^2$. The media was changed twice a day. The proliferation of hDFs was measured by alamarBlue on days 7 and 14 by measuring the fluorescence at 595 nm (excitation at 555 nm).

The three-dimensional distribution of hDFs in the hydrogels was visualized by confocal microscopy. After 14 days from the initial seeding, the samples were fixed in 4% formaldehyde in PBS overnight and stained with ActinRed 555 to stain the actin cytoskeleton of hDFs. Z-section images were obtained using a confocal microscope (Nikon AIR HD, Melville, NY), and 2D projection, 3D images, and cross-sectional images were obtained using ImageJ.

Figure 6A:
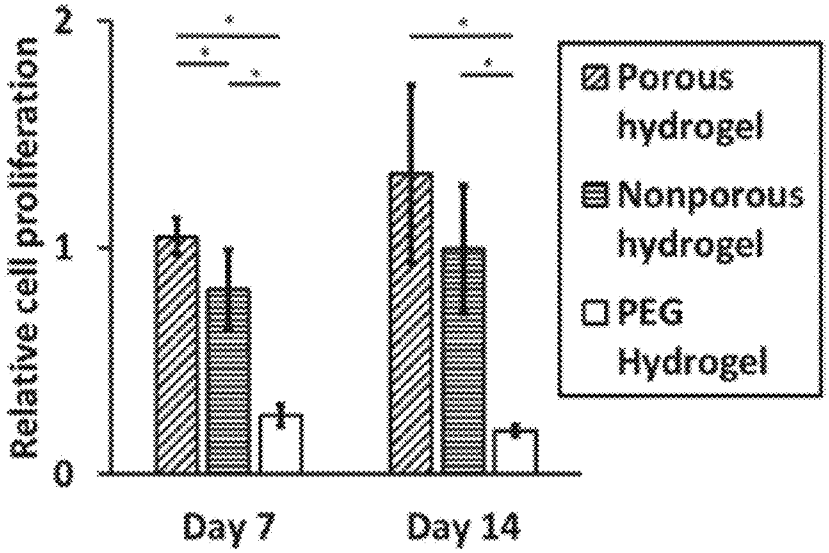
FIG. 6A-B provides bar graphs and photomicroscopic images illustrating cell proliferation on embodiments of hydrogels.

As illustrated in FIG. 6A, proliferation of hDFs on the porous hydrogel was higher than on the nonporous hydrogel over the two week period, and there was no statistical significance between the two groups at week 2. Various studies have shown that mTG-cross-linked nonporous gelatin hydrogel supports cell adhesion and proliferation [Maddaus, A. et al., (2016) Biointerphases 11 (4), 041002 and Yang, G. et al., (2018) Sci. Rep. 8 (1), 1616]. The fact that the macroporous gelatin hydrogel resulted in a higher cellular proliferation than the nonporous gelatin hydrogel proves its significant bioactivity properties and its potential use in biological systems, such as for wound healing. hDF proliferation on the gelatin macroporous hydrogel is comparable to PEG-based macroporous hydrogel, which also supported robust proliferation of hDFs encapsulated in the hydrogel [Griffin, D. R.; et al., (2015) Nat. Mater. 14 (7), 737].

Figure 6B:
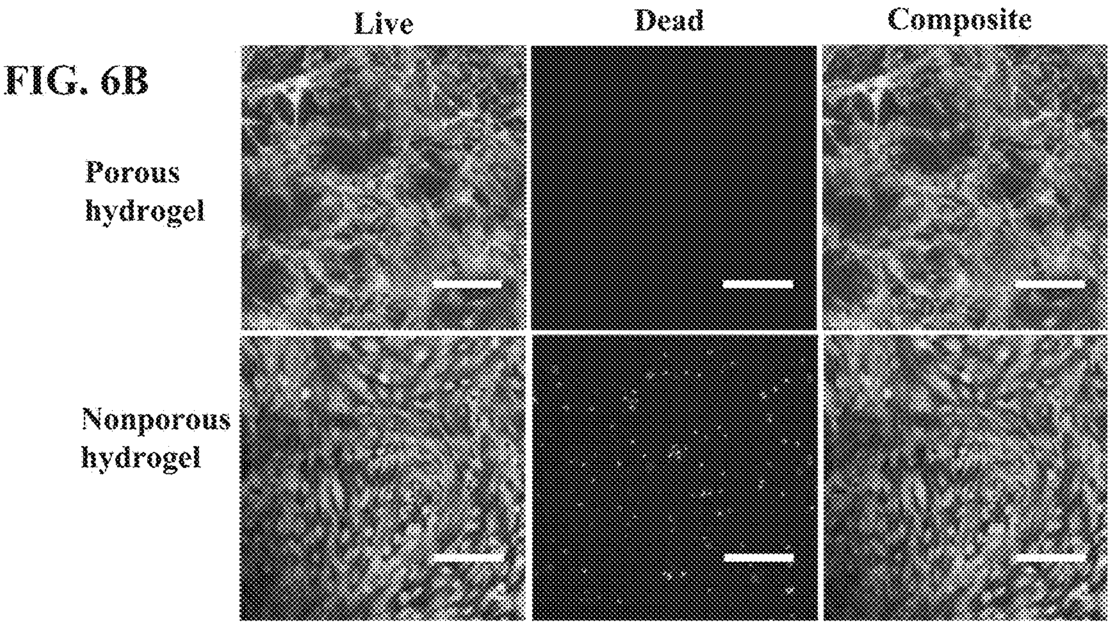

The advantage of using gelatin as a base material for an injectable macroporous hydrogel as opposed to other synthetic polymers is highlighted by comparing the proliferation of hDF on a nonporous PEG hydrogel created by cross-linking maleimide functionalized four-arm polyethylene glycol (20 kDa) by dithiothreitol. Hydrogels made of synthetic polymers typically do not support cell adhesion or proliferation without chemical modifications with bioactive moieties, such as cell adhesive RGD peptides [Burdick, J. A. & Anseth, K. S. (2002) Biomaterials 23 (22), 4315-4323; Groll, J. et al., (2005) J. Biomed. Mater. Res., Part A, 74 (4), 607-617; and Weber, L. M. et al., (2007) Biomaterials 28 (19), 3004-3011]. In contrast, the gelatin-based porous hydrogels of the present disclosure do not require any chemical modifications to promote cell adhesion and proliferation because of innate cell adhesive ligands, such as RGD, present in gelatin. A live/dead assay showed that the cells in both porous and nonporous hydrogels were viable (as illustrated in FIG. 6B).

Figure 7A:
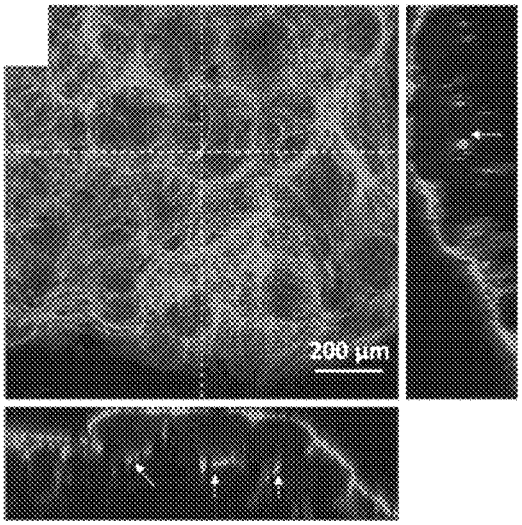
FIG. 7A-B provides photomicroscopic images showing maximum intensity projection of confocal microscope images.
Figure 7B:
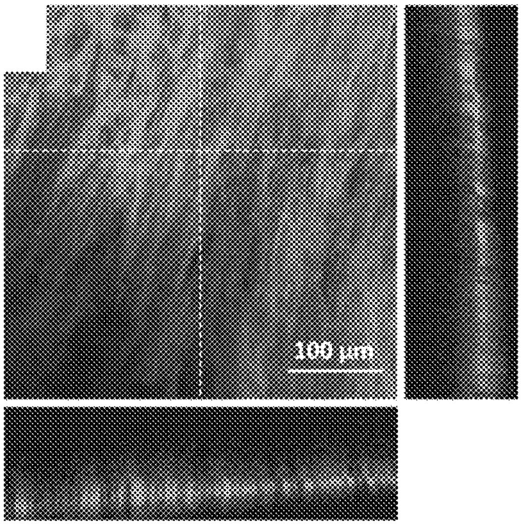

When the hDFs were stained for actin cytoskeleton and visualized by confocal microscopy, some hDFs were found to grow beyond the first layer of the gelatin microgels despite the fact that all cells were initially added on the hydrogel surface (as illustrated in FIG. 7A). This shows that the gelatin macroporous hydrogel not only supports cell adhesion and proliferation, but also allows cell migration through the pores. This is a beneficial feature of the macroporous gelatin hydrogel because cell migration is an essential phenomenon during the wound healing process. In contrast, the cells on the nonporous gelatin hydrogel grew exclusively on the surface of the hydrogel (as illustrated in FIG. 7B). Due to the small polymer mesh size, the hydrogel must be degraded first for the cell migration into the nonporous hydrogel, which was not observed during the time frame of this testing.

Example 6

Application of Hydrogel to Porcine Cornea Tissues Ex Vivo

Fresh pig eyeballs were sterilized by immersion in povidone-iodine and rinsing several times with sterile PBS. Cornea tissues were collected from the eyeballs using surgical scissors. A hole was created in the middle of the cornea using a biopsy punch (8 mm in diameter). The hole in the cornea was filled by injecting either gelatin microgel solution mixed with mTG, or plain gelatin solution mixed with mTG, to create a porous or nonporous hydrogel, respectively. The assembly was incubated for about 1 hour at 37° C. for curing, after which DMEM supplemented with FBS and pen/strep was added. The tissue-hydrogel assembly was fed daily for 14 days before fixation in formaldehyde. The corneas were stained with ActinRed555 and DAPI and imaged by a confocal microscope.

Figure 8A:
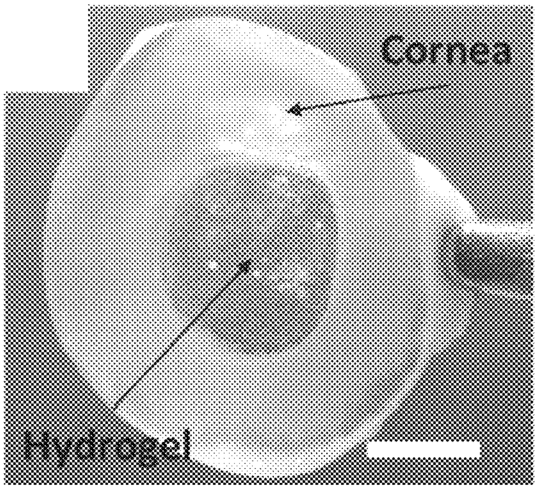
Figure 8B:
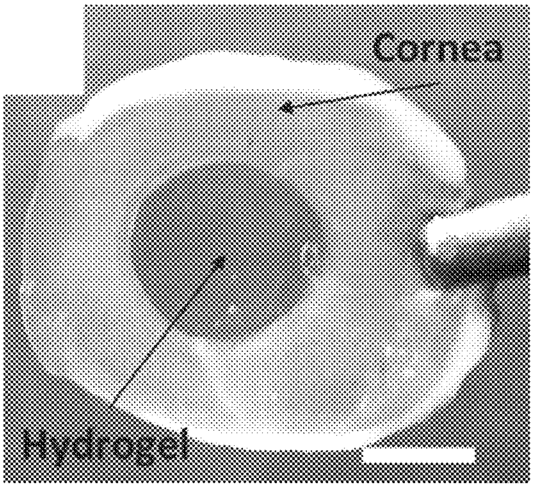
Figure 8C:
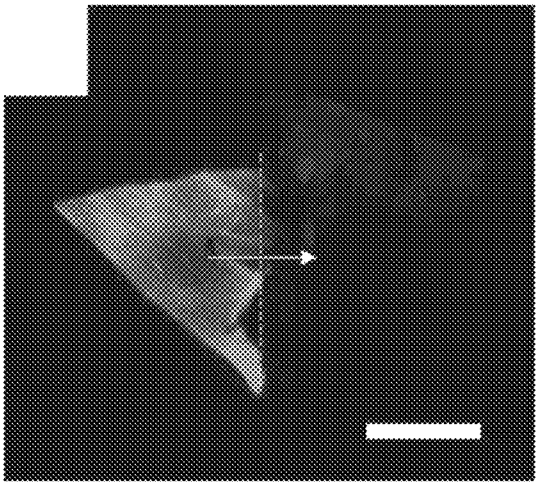
Figure 8D:
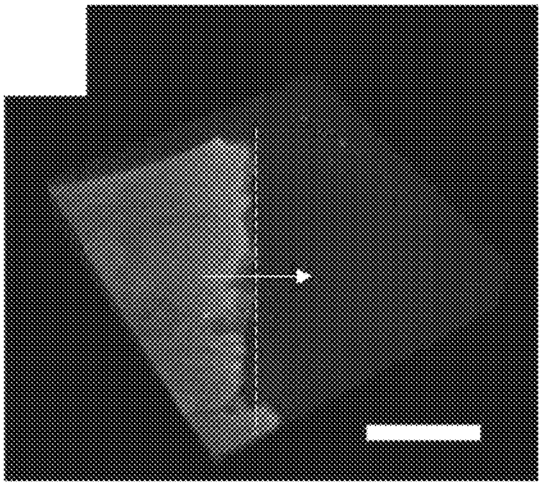
Figure 8E:
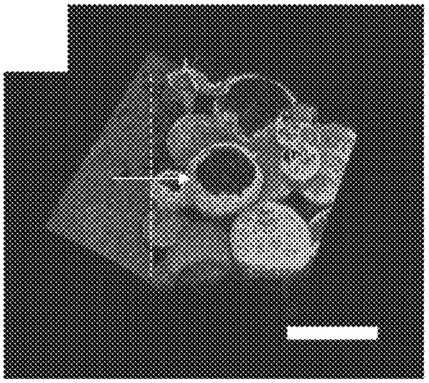
Figure 8F:
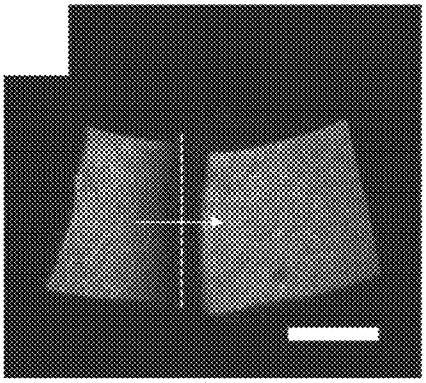
Figure 8G:
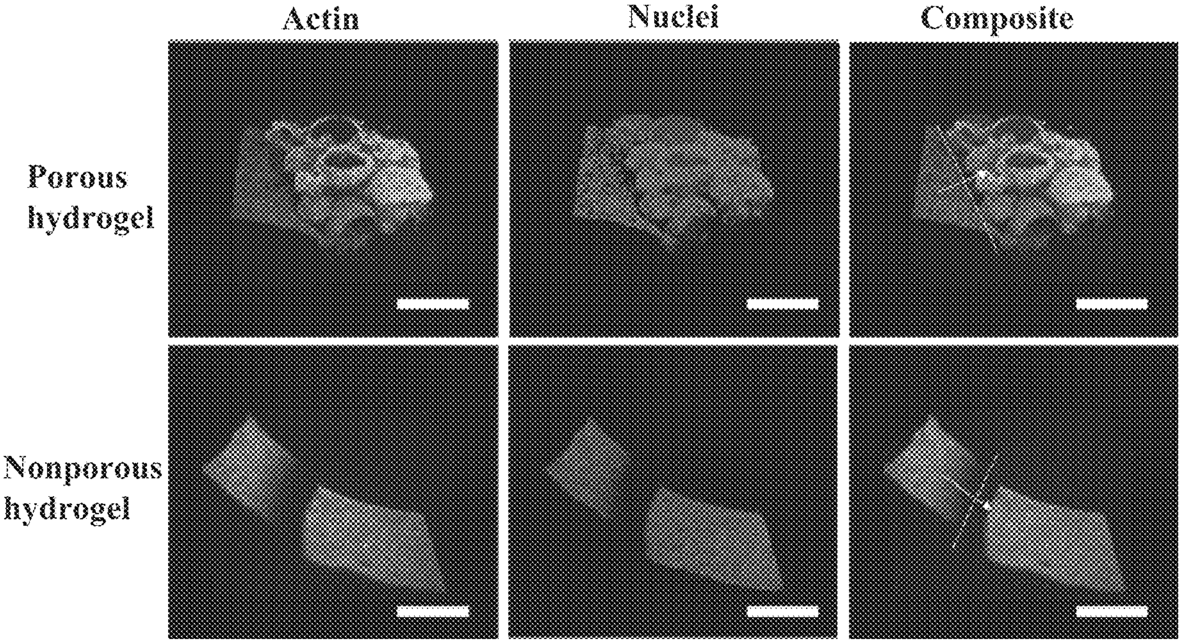
Figure 10:
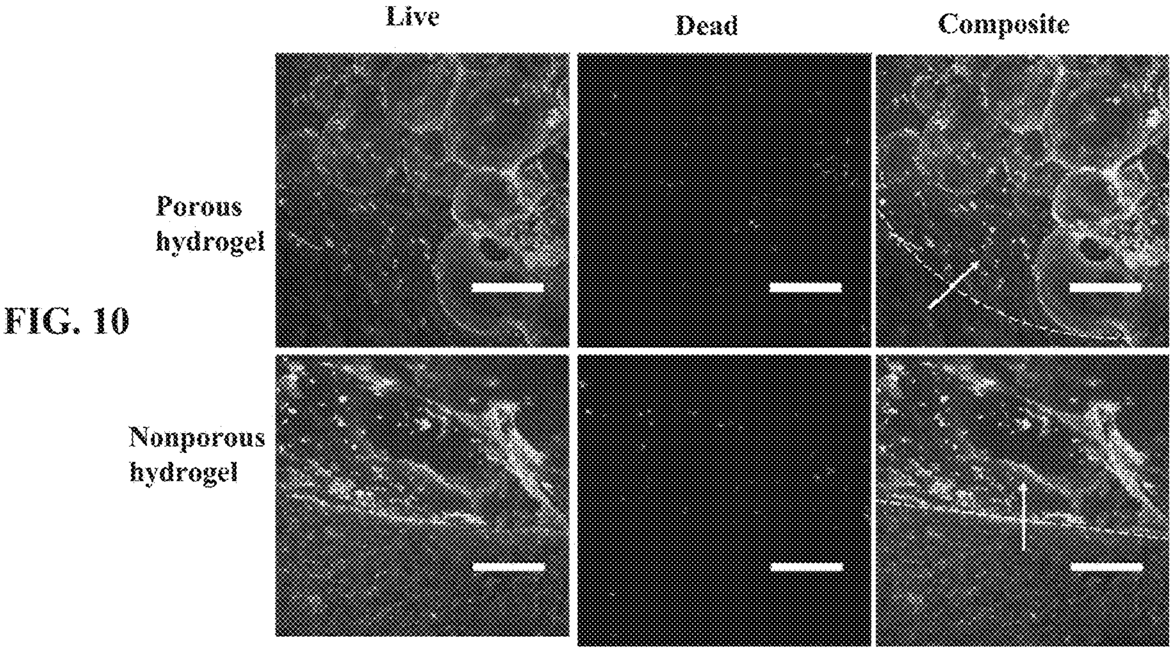
FIG. 10 provides maximum intensity projections of confocal microscope images illustrating cell viability at an interface between porcine cornea and porous/nonporous hydrogels on day 14. Viable cells were stained green by calcein-AM, and dead cells were stained red by ethidium homodimer-1. Dotted lines indicate a cornea-microgel interface with arrows indicating a direction from the cornea to the hydrogel. The scale bar is 200 μm.

The hydrogels stably adhered to the tissue through the action of mTG during the 2 week span of tissue culture (as illustrated in FIG. 8A-B). On day 0, cells were found only in the cornea tissue as no cells were present in the hydrogels (as illustrated in FIG. 8C-D). On day 14, the hydrogel phase was densely populated by the cells, mainly the corneal epithelial cells that migrated from the cornea tissue (as illustrated in FIG. 8E-J). As in the in vitro culture of hDFs, cells were found not only on the hydrogel surface but also inside the void space of the porous hydrogel, whereas migrated cells were found exclusively on the surface of the nonporous hydrogel (as illustrated in FIG. 9A-B). A live/dead assay showed that the majority of the cells in the cornea tissue and the hydrogels (both porous and nonporous) were viable (as illustrated in FIG. 10).

Porous gelatin hydrogel may, in at least some embodiments, only be used for small-sized peripheral corneal wounds due to its low transmittance (about 30%) in the visible range. Porcine cornea was chosen as a model tissue for its ready accessibility and ease of tissue culture [Salvador-Culla, B. et al., (2016) Vis Sci. Techn 5 (2), 17 and Wang, L. et al., (2011) Invest. Ophthalmol. Visual Sci. 52 (10), 7392-7399]. The results herein point to the potential of the herein disclosed porous hydrogel formulations being used to facilitate the wound healing process in non-ocular tissues (e.g., skin) as well by allowing cell migration and proliferation within the hydrogel.

Example 7

Controlled Release of FITC-BSA and Platelet-Derived Growth Factor (PDGF)

Various growth factors play essential roles during the wound healing process. For example, platelet-derived growth factor (PDGF) is released during wound healing and induces the proliferation of fibroblasts for the secretion of a new extracellular matrix (ECM) [Bonner, J. C. et al., (1990) J. Cell. Physiol. 145 (1), 1-8; Deuel, T. F. et al., (1991) Annu. Rev. Med. 1991, 42, 567-584; and Agren, M. S. et al., (1999) J. Invest. Dermatol. 112 (4), 463-469]. A hydrogel formulation to facilitate wound healing, therefore, should have the capability of controlled release of growth factors.

Figure 11A:
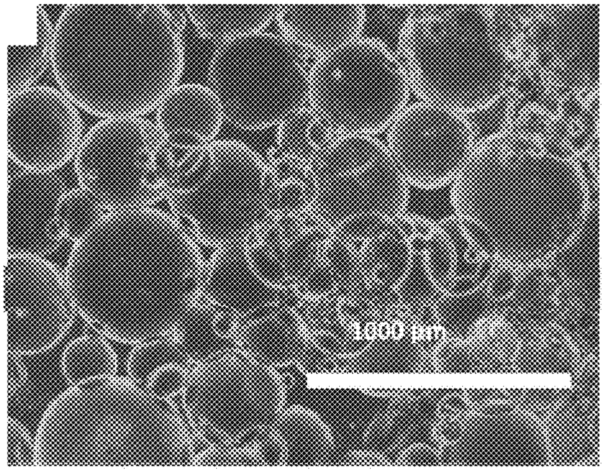
FIG. 11A-C provides photomicroscopic images and a graph illustrating elements of FITC-BSA-loaded gelatin microgels.
Figure 11B:
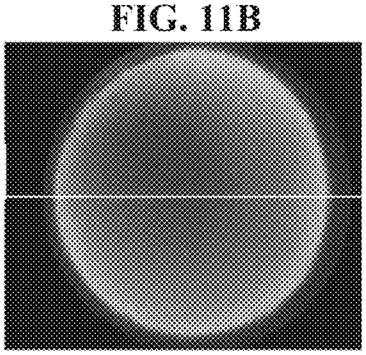
Figure 11C:
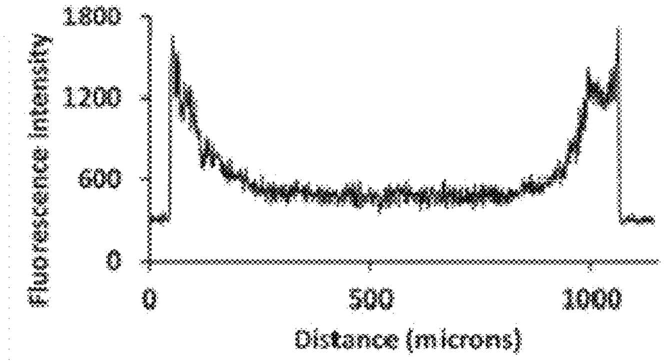

In order to understand the nature of protein loading in porous hydrogels of various embodiments of the present disclosure, gelatin microgels were incubated in a FITC-labeled bovine serum albumin (FITC-BSA) solution (about 100 μg/mL) for about 48 hours at room temperature (e.g., about 20° C. to about 25° C.). After the supernatant was removed, the distribution of FITC-BSA within the gelatin microgels was visualized with a confocal microscope. The proteins were found mainly on the surface of the gelatin microgels as the diffusion of the protein occurred through the surface (as illustrated in FIG. 11A-C). PDGF loading into the microgels was achieved using the same method except that the concentration of PDGF was reduced to about 20 μg/mL. A PDGF-loaded porous hydrogel was formed by mixing these gelatin microgels with unloaded gelatin microgels at a 1:9 ratio (v/v) and cross-linking it using mTG. The PDGF-loaded nonporous hydrogel was created by adding PDGF to a gelatin solution, which was cross-linked by mTG. After the hydrogels were formed, the release of PDGF was measured at days 1, 2, 3, 7, and 14 by an enzyme-linked immunosorbent assay (ELISA).

Figure 12:
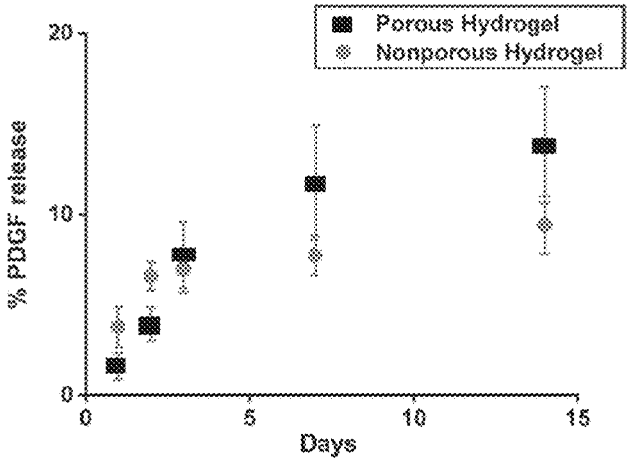
FIG. 12 is a graph illustrating a cumulative release profile of platelet-derived growth factor (PDGF) from hydrogels, in accordance with embodiments of the present disclosure.

For both the porous and nonporous hydrogels, the overall release of PDGF was inefficient over 2 weeks (about 13% and about 9% release of the initial loading from the porous and nonporous hydrogel, respectively) (as illustrated in FIG. 12). The reason for such inefficient release is likely due to covalent immobilization of PDGF to the hydrogels by the action of mTG during the cross-linking process. Covalent attachment of proteins within the hydrogel during the cross-linking process is common for covalently cross-linked injectable hydrogels. It is also known that the positively charged growth factors are strongly bound to negatively charged gelatin hydrogels, making the growth factor release inefficient even if the loading is performed after the covalent cross-linking of the hydrogel. Nonetheless, the porous hydrogel released a higher amount of PDGF at a steadier rate than the nonporous hydrogel. Considering that the gelatin hydrogels degrade in the presence of collagenases and there exists various kinds of collagenases and gelatinases in vivo [Thrailkill, K. M. et al., (2005) Clin. Chem. Lab. Med. 43 (12), 1392-1399], it is expected that the growth factor release from the gelatin hydrogels will be more efficient in vivo with the degradation of the hydrogel [Nguyen, A. H. et al., (2015) Acta Biomater. 13, 101-110].

Example 8 hDF Proliferation with Controlled Release of PDGF from Hydrogels hDFs were seeded on 24-well plates with a seeding density of 1500 cells/cm$^2$. On day 2, PDGF-loaded porous and nonporous hydrogels were added to the cell culture through transwell inserts with semipermeable membranes. Proliferation of hDFs was measured by an alamarBlue assay on day 7.

Figure 13A:
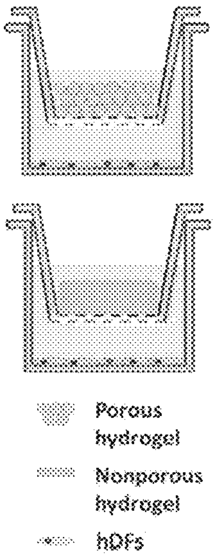
FIG. 13A-B provides a schematic diagram and a bar graph illustrating effects of porous and nonporous hydrogels on hDF proliferation.
Figure 13B:
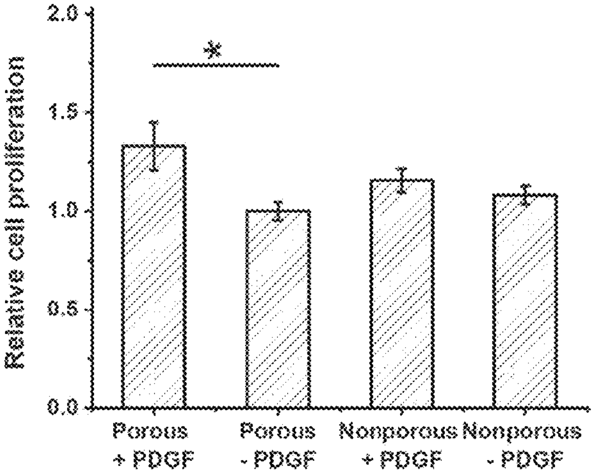

When the PDGF was released into the culture medium of hDFs for 2 weeks through semipermeable membranes (as illustrated in FIG. 13A), the cellular proliferation increased by 1.3 times for the porous hydrogel when compared to the culture without PDGF (p=0.039) (as illustrated in FIG. 13B). No significant differences were observed at earlier time points. PDGF release from the nonporous hydrogel also increased the proliferation of hDFs, but there was no statistical significance compared to the culture without PDGF (p=0.900).

Example 9

UV Irradiated Macroporous Hydrogel

Figure 14:
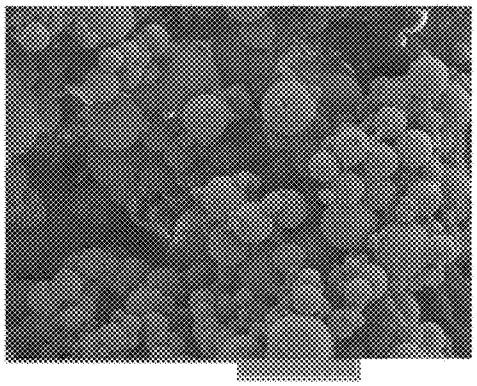
FIG. 14 is a SEM image of a macroporous hydrogel assembled by ultraviolet (UV) irradiation on gelatin/methacrylated gelatin (GelMA) microgel. Scale bar=200 μm.

Gelatin was mixed with GelMA (e.g., in a mass ratio of 2:1) during microgel synthesis using the water-in-oil method described herein. The resulting microgels were mixed with a photoinitiator (e.g., Irgacure 2959, 0.05%) and mTG, and cured by UV irradiation. Dual cross-linking by mTG and UV irradiation was observed. UV irradiation on the GelMA-containing microgels enabled rapid cross-linking, and the enzymatic cross-linking by mTG allowed the resulting hydrogel to adhere to human tissues. Within 2 minutes of UV irradiation, the microgels formed a stable bulk hydrogel (as illustrated in FIG. 14).

Figure 15A:
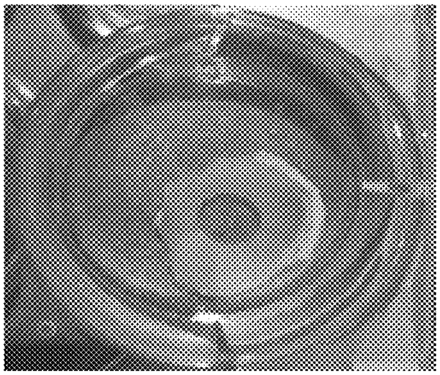
FIG. 15A-D provides photographic images of results from porcine cornea experiments.
Figure 15B:
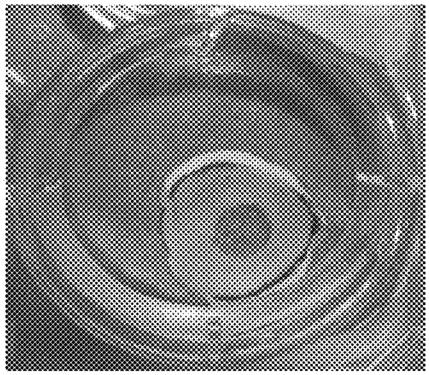
Figure 15C:
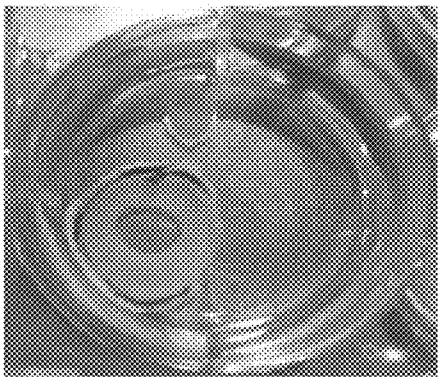
Figure 15D:
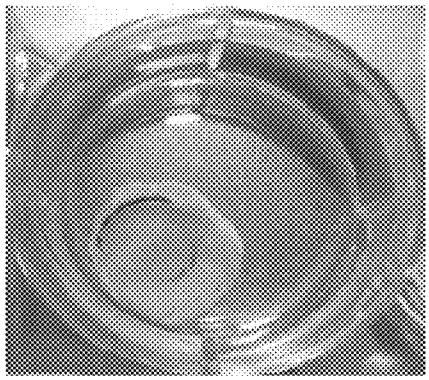

The foregoing formulation was applied on a small hole (about 8 mm in diameter) in porcine corneas to test (1) if a stable hydrogel forms and (2) if the hydrogel adheres to the cornea tissue. Porcine corneas were used because of their ready availability. However, one skilled in the art will appreciate that the foregoing formulation may be applied to any human (or animal) tissues. FIG. 15A-D show that the hydrogel formed by both UV-cross-linking and mTG achieves both of the foregoing objectives of this testing. If the hydrogel is formed with UV cross-linking only (without mTG), as illustrated in FIG. 15C, a stable hydrogel forms, but it does not adhere to the tissue.

Figure 16A:
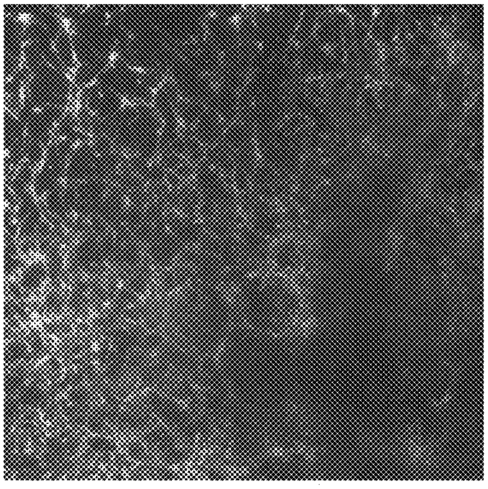
FIG. 16A-B provides photomicroscopic images of hDFs. Images show 2-dimensional projections of 3-dimensional confocal microscope images of hDFs encapsulated in a macroporous hydrogel (FIG. 16A) and of hDFs encapsulated in a nonporous hydrogel (FIG. 16B). Viable and dead cells were labeled with green and red fluorescence, respectively.
Figure 16B:
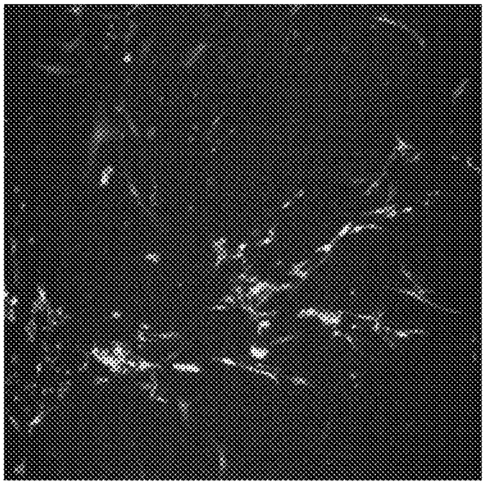

Testing was performed to determine if a UV irradiation method could be used to encapsulate human cells. Gelatin/GelMA microgels were mixed with hDFs, and mTG and a photoinitiator were added, which was then followed by about 2 minutes of UV irradiation. Rapid cell growth within the resulting macroporous hydrogel was observed as compared to a nonporous hydrogel (produced using the same gelatin/GelMA, but the hydrogel was formed by cross-linking gelatin/GelMA solution instead of gelatin/GelMA microgels) (as illustrated in FIG. 16A-B.

Example 10

Cell Encapsulation within Interstitial Space

For encapsulation of hDFs, hDFs, gelatin microgels, and mTG were mixed at a concentration of about 600 cells/μL. The final concentration of gelatin microgels and mTG was about 8.3% (w/v) and about 3.3% (w/v), respectively. hDFs in nonporous hydrogel were created by mixing the same amount of cells with a gelatin solution (concentration equal to about 8.3% (w/v)) with mTG (concentration equal to about 3.3% (w/v)). The construct was incubated for about 30 minutes at about 37° C., after which culture media was added. The cells were fed daily.

The cells encapsulated within the macroporous hydrogel (the hydrogel made by gelatin microgels) showed significant spreading around the microgels, even from day 1 (as illustrated in FIG. 17A). By day 4, the interstitial space was full of hDFs, demonstrating robust proliferation of hDFs in the hydrogel (as illustrated in FIG. 17B-C). On the contrary, most of the hDFs in the nonporous hydrogel were still round, indicating they were trapped in the hydrogel mesh, and did not proliferate as much (as illustrated in FIG. 17D).

Example 11

Osteogenic Differentiation of Adipose Stem Cells

The same cell encapsulation method, described above with respect to encapsulating hDFs, was used to encapsulate human adipose stem cells. Human adipose stem cells have the potential to differentiate into osteoblasts, chondrocytes, and adipocytes. The encapsulated human adipose stem cells (both in macroporous and nonporous hydrogels) were cultured for one week in growth media (which keeps the human adipose stem cells in an undifferentiated state and allows them to proliferate), after which the media was switched to an osteogenic differentiation media. Thereafter, the human adipose stem cells were cultured for an additional two weeks.

Confocal microscope images (shown in FIG. 18A-B) were taken after staining the human adipose stem cells with live/dead assay. The green and red fluorescence indicate the live and dead human adipose stem cells, respectively. As shown, human adipose stem cells spread well and grew in a much larger number in the macroporous hydrogel compared to the human adipose stem cells in the nonporous hydrogel.

Example 12

Calcium Deposition (Alizarin Red)

Figures 19A, 19B:
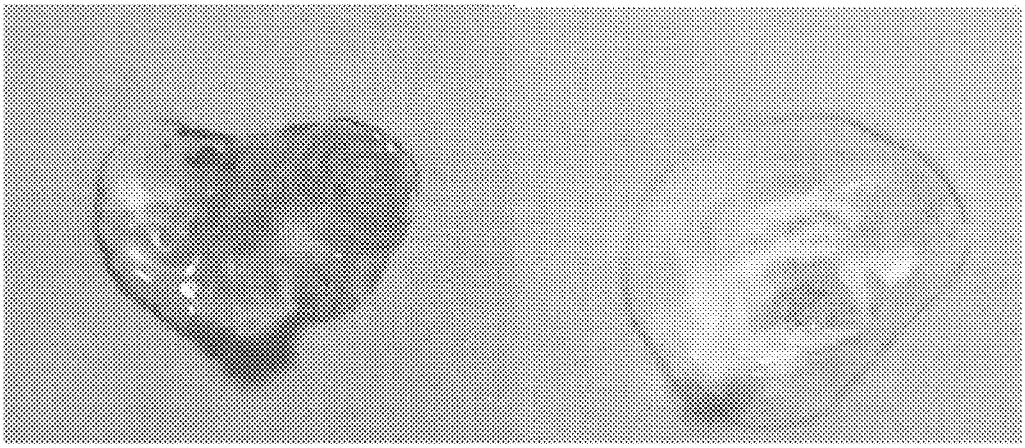
FIG. 19A-B provides camera images of porous (FIG. 19A) and nonporous (FIG. 19B) hydrogel with adipose stem cells. The adipose stem cells were cultured for three weeks as described for FIG. 18A-B, followed by an alizarin red assay to stain calcium deposits in the cells with strong red.

To visualize osteogenic differentiation of adipose stem cells, Alizarin Red assays were performed. Alizarin red dye solution (about 40 mM) was added to cell-encapsulating hydrogel, which was then incubated for about 30 minutes. The hydrogels were washed three times, and the images of FIG. 19A-B were taken using a digital camera. The red stain indicates calcium deposition. The porous hydrogel was stained with strong red (see FIG. 19A), whereas the nonporous hydrogel was not (see FIG. 19B). Although both hydrogels were soft and it is well-known that such soft hydrogels are not conducive for osteogenic differentiation of adipose stem cells, the adipose stem cells in the porous hydrogel nonetheless showed osteogenic differentiation.

This is expected to be a result of an un-restraining 3-dimensional culture environment provided by the macropores of the porous hydrogel.

Example 13

HUVECs in Porous Hydrogel

Figure 20:
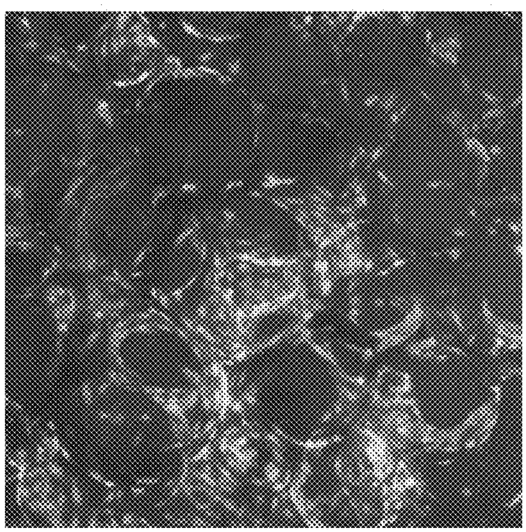
FIG. 20 provides a 2-dimensional rendition of a 3-dimensional confocal image of a live/dead assay on human umbilical vein endothelial cells (HUVECs) encapsulated in porous hydrogel.

HUVECs were encapsulated in porous hydrogel, which was made by curing gelatin microgels in a same condition the hDFs and adipose stem cell experimentations above. After two weeks of culture, the HUVECs were stained with live/dead assay and visualized using confocal microscopy. Overall, the HUVECs spread and proliferated well in the interstitial space (as illustrated in FIG. 20). It was also observed that, in some areas, the HUVECs formed tubular enclosures (e.g., a blood vessel-like structure). The tubular enclosures were automatically generated during microgel assembly.

Example 14

Proliferation of HUVECs

Figure 21A:
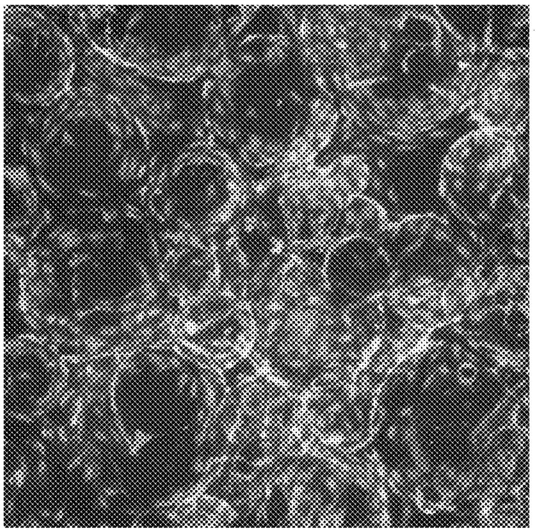
FIG. 21A-B provides photomicroscopic images of 2-dimensional renditions of a 3-dimensional confocal images of a live/dead assay on human umbilical vein endothelial cells (HUVECs) encapsulated in porous hydrogel (FIG. 21A) or in nonporous hydrogel (FIG. 21B), after two weeks of encapsulation.
Figure 21B:
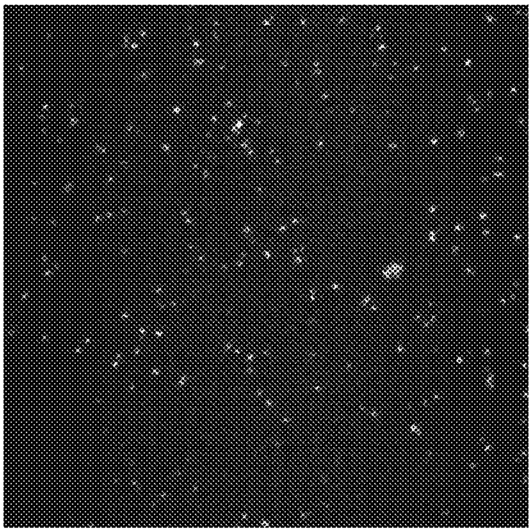

FIG. 21A-B are examples of live/dead assay with confocal microscopy, showing a significant contrast between HUVECs encapsulated in porous hydrogel (see FIG. 21A) and nonporous hydrogel (see FIG. 21B). The HUVECs in the porous hydrogel proliferated significantly, with few dead cells. However, the HUVECs in the nonporous hydrogel did not spread (spherical in shape) and many more dead cells were observed.

Example 15

Injectable Cardiac Patch

A cardiac patch is made of cardiomyocytes embedded in a 3-dimensional scaffold, and its purpose is to be implemented on a damaged cardiac tissue to aid the contractile function of the heart. Typically, this requires open heart surgery. With an injectable cardiac patch, open heart surgery may be unnecessary. A factor in cardiac patches is electrical/biochemical coupling among the cardiomyocytes. Such coupling is achieved through "gap junction." It is not trivial to provide an environment where the cardiomyocytes can make efficient gap junctions.

Figure 22:
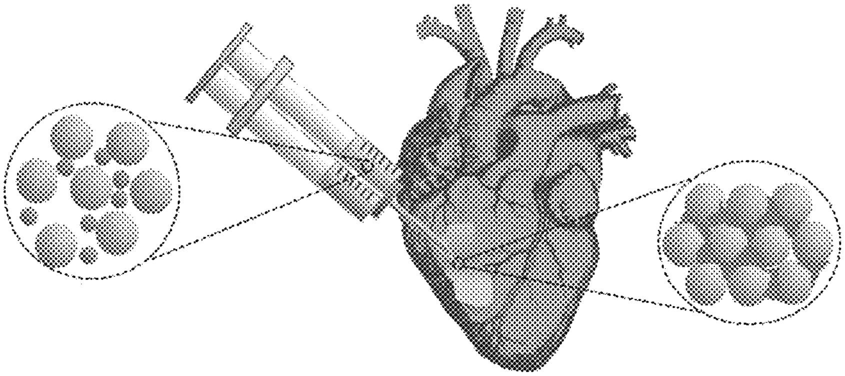
FIG. 22 is a conceptual diagram of an injectable cardiac patch.
Figure 23A:
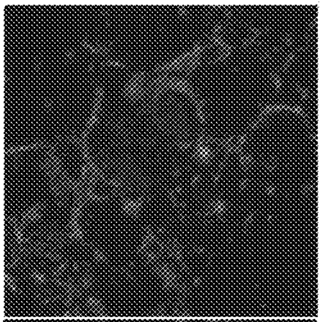
FIG. 23A-D provides photomicroscopic images of HL-1 cardiomyocyte cells in porous hydrogel after three days of culturing.
Figure 23B:
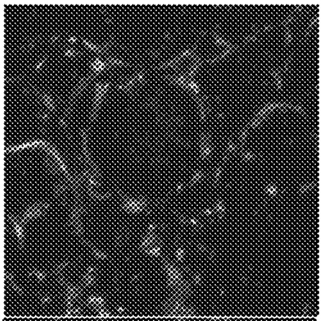
Figure 23C:
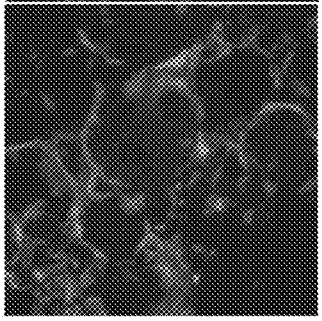
Figure 23D:
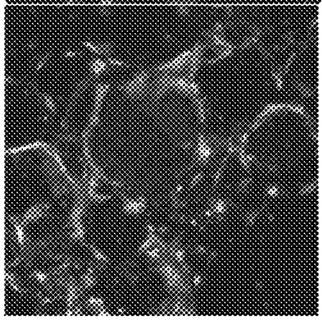
Figure 24A:
FIG. 24A-D provides photomicroscopic images of HL-1 cardiomyocyte cells in porous hydrogel after seven days of culturing, in accordance with embodiments of the present disclosure.
Figure 24B:
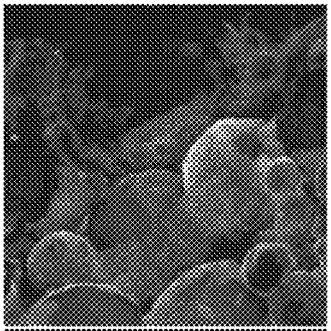
Figure 24C:
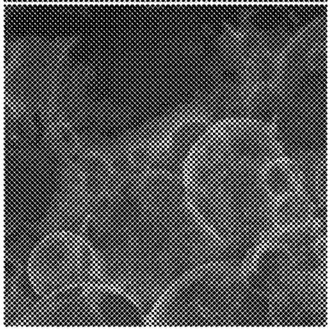
Figure 24D:
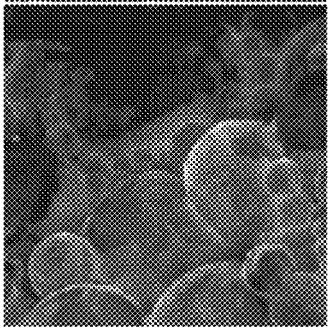

An injectable porous hydrogel of the present disclosure may reduce the necessity of open heart surgery, as well as provide an environment where the cardiomyocytes can make efficient gap junctions. As illustrated in FIG. 22, as cardiomyocyte cell are encapsulated in a porous hydrogel of the present disclosure, the cardiomyocytes can make physical contacts with each other through interconnected pores of the hydrogel. This is in line with the foregoing encapsulation studies of other cell types, in which the cells spread significantly and proliferate well in the interstitial space of porous hydrogel.

HL-1 cells (mouse cardiomyocyte cell line) were cultured in a porous hydrogel using the same conditions as described above. The construct was cultured for one week. On days 3 and 7, the cells were fixed and stained with 3 fluorescent colors. DAPI stained the nuclei with blue fluorescence, rhodamine-phalloidin stained the actin cytoskeleton with red, and connexin 43 (the gap junction proteins) was stained green using antibodies.

Even on day 3 (as illustrated in FIG. 23), the cells were found to have spread significantly inside the interstitial pores, and gap junction protein (connexin 43) was significantly expressed in most of the cells, which indicate that the cells were making physical contacts and forming the electrical/biochemical coupling as early as day 3. The results were even more promising on day 7 (as illustrated in FIG. 24).

Conclusion—Examples 1-15

Addition of enzyme, more specifically transglutaminase, and more specifically mTG, to gelatin microgels induced covalent cross-links within and between the gelatin microgels, forming a bulk macroporous hydrogel. This injectable hydrogel did not require any chemical modification before gelation. The hydrogel was noncytotoxic to hDFs and allowed adhesion and proliferation of hDFs on the hydrogel surface and cell migration into the hydrogel pores. Upon injection into a hole in porcine corneal tissue, a significant number of cells from the surrounding cornea tissue migrated to the porous hydrogel and proliferated both on the surface and in the pores of the hydrogel. Controlled release of PDGF over 2 weeks was achieved using the hydrogel, which enhanced the proliferation of hDFs. The fact that this simple and low-cost hydrogel allows cellular adhesion and migration into the porous structure indicates its potential applications in wound healing and tissue engineering.

Example 16

Fast-Curing Injectable Microporous Hydrogel and Use for In Situ Cell Encapsulation Materials and Methods All materials were purchased from Sigma-Aldrich (St. Louis, MO) unless specified. Microbial transglutaminase (mTG) was purchased from Ajinomoto (Fort Lee, NJ). Sterile phosphate buffer saline (PBS, pH 7.4) was purchased from Gibco (Carlsbad, CA). Human dermal fibroblasts (hDFs) were purchased from Lonza (Portsmouth, NH). Cell Viability kit, Dulbecco's Modified Eagle's Medium (DMEM), fetal bovine serum (FBS), 10,000 U/ml penicillin/streptomycin (pen/strep), alamarBlue, LDH assay, and ActinRed 555 were purchased from Invitrogen (Frederick, MD). Fresh pig eyeballs were obtained from Visiontech (Sunnyvale, TX).

Synthesis of Gelatin/GelMA Composite Microgels

The gelatin/GelMA composite microgels were prepared using a method similar to the previously reported method [Y. Li, J. et al., (2012) Chem. Soc. Rev., 41, 2193-2221]. Due to the photoactive nature of GelMA, all procedures involving GelMA were performed in the dark. A 2:1 mixture (by weight) of gelatin (type A, from bovine and porcine bones, bloom 300 g) and gelatin methacryloyl (bloom 300 g, 80% degree of substitution) was dissolved in 20 mL of deionized water at 50-55° C. to make a total 10% (w/v) aqueous solution. This solution was added dropwise to 200 mL of olive oil at 50-55° C. and stirred for 1 hour. The temperature of the mixture was lowered to reach room temperature for 30 min with stirring. Then the mixture was placed in an ice-water bath for an additional 30 min with stirring to solidify the microgels by inducing physical cross-linking. To precipitate the microgels, 100 mL of pre-cooled acetone (4° C.) was added to the mixture with stirring for 30 min in the ice-water bath. The microgels were separated from the olive oil and acetone by vacuum filtration and further washed with two 60 mL aliquots of precooled (4° C.) acetone. The microgels were immediately frozen at −80° C., lyophilized, and kept dry until used.

Characterization of Microgels

Microgels were visualized by scanning electron microscopy (SEM) (Tescan Lyra3 GMU FIB SEM, Brno, Czech Republic) and optical microscopy (EVOS XL, Life Technologies, Carlsbad, CA). Prior to imaging, lyophilized microgels were coated with gold/palladium to avoid charging. For quantification of hydrated microgel size distribution, 20 μL of a dilute microgel suspension in PBS was observed using an optical microscope. Size distribution of microgels was obtained from the SEM and optical microscope images using ImageJ.

Bulk Hydrogel Formation

Microporous hydrogels were made by mixing gelatin/GelMA composite microgels (10% w/v) with the photoinitiator (PI) (Irgacure 2959) in PBS (0.5% or 0.05% w/v). Ascorbic acid was added to a final concentration of 0.005% (w/v) to minimize cytotoxicity during the UV irradiation. This mixture was mixed with 20% (w/v) mTG in PBS in a 5:1 ratio. The final concentration of gelatin/GelMA and mTG was 8.3% and 3.3%, respectively. UV light (365 nm) was applied for 2.5 mins to induce photoinitiated cross-linking. Nonporous hydrogels were made by the same method except that a gelatin/GelMA solution was used instead of gelatin/GelMA microgels.

Characterization of Hydrogels

After the hydrogels were formed, their detailed structure was visualized with SEM. Prior to SEM imaging, the hydrogels were dehydrated through an ethanol series (30%, 50%, 60%, 70%, 80%, and 90% once each, and then 100% twice) before being dried by critical point drying and coated with gold/palladium.

The viscoelastic properties of the hydrogels were characterized by rheometry (TA Instruments AR 550, New Castle, DE). A gelatin/GelMA microgel suspension was made in PBS containing the PI and ascorbic acid as previously described. Cross-linking was initiated by different conditions for 2.5 min before being placed under a planar stainless-steel geometry. The gelation kinetics were observed at 37° C., with an oscillatory stress of 1 Pa at 10 rad/s. Once gelation was completed, a frequency sweep was performed, increasing angular frequency from 0.1 to 100 rad/s with an oscillatory stress of 1 Pa at 37° C. Then, temperature sweep was performed. Temperature was gradually increased from 5 to 45° C. with an oscillatory stress of 1 Pa at 10 rad/s. All measurements were performed in the linear viscoelastic regime.

The enzymatic degradation of microporous gelatin/GelMA hydrogels and gelatin/GelMA microgels was examined by incubating in collagenase type II solution (concentration=0.5 U/mL) at 37° C. At different time points (0 h, 4 h, 24 h), the hydrogels and microgels were collected, lyophilized, and weighed to calculate the fraction of remaining solids content.

Tissue Adhesion of the Hydrogels

Porcine corneas were used to examine the tissue adhesion capability of the hydrogels. Corneas were collected from freshly obtained pig eyeballs using surgical scissors. A hole was created in the middle of the cornea using a biopsy punch (diameter=8 mm) and was filled by injecting microgel solution prepared as previously described. After 2.5 min of cross-linking under different conditions, the tissue/hydrogel construct was transferred to 45° C. PBS, to test for gelation and tissue adhesion.

Cell Encapsulation and Characterization

Human dermal fibroblasts (hDFs) were cultured in T75 flasks using DMEM, supplemented with FBS and pen/strep. Cells of passage 4 were used for all experiments. Prior to cell encapsulation, the gelatin/GelMA microgels and GelMA powders were sterilized by incubation in 70% ethanol overnight, at 4° C. Gelatin, mTG, Irgacure 2959, and ascorbic acid solutions were sterilized by syringe filtration. For encapsulation, hDFs were mixed with microgel suspension or gelatin/GelMA solution in media, containing mTG, PI, and ascorbic acid, followed by 2.5 mins of UV irradiation. Hydrogels were then incubated at 37° C. for 1 hour. The encapsulated cells were cultured in the media described above in Example 16.

The three-dimensional distribution of hDFs in hydrogel was visualized by confocal microscopy (Nikon AIR HD, Tokyo, Japan) on days 1 and 7 post-encapsulation using a live/dead cell viability kit, which stains living cells green (by calcein-AM) and dead cells red (by ethidium homodimer). To visualize the details of cell spreading and morphology inside the hydrogel, each sample was fixed in 4% paraformaldehyde (in PBS) overnight and stained with ActinRed 555. Z-stacked images were then obtained using the confocal microscope, and 2D projections were generated from Z-stacks using ImageJ. Sphericity, viability and proliferation were calculated using the plug-ins provided by ImageJ.

LDH assay was performed to assess cytotoxic effects related to the encapsulation process. Cells seeded on well plates were used for maximum LDH controls, and hydrogels formed without encapsulated cells were used as negative controls. The culture media were taken on day 1 and 7 for analysis.

Statistical Analysis

All data is represented as means, and all error bars represent standard deviations. All experiments were run with at least n=3 samples. Statistical significance was determined using a student's t-test, when comparing two groups, or Tukey's HSD post hoc test, in experiments comparing more than two groups. $p<0.05$ was considered statistically significant.

Results/Discussion Example 16

Figure 25A:
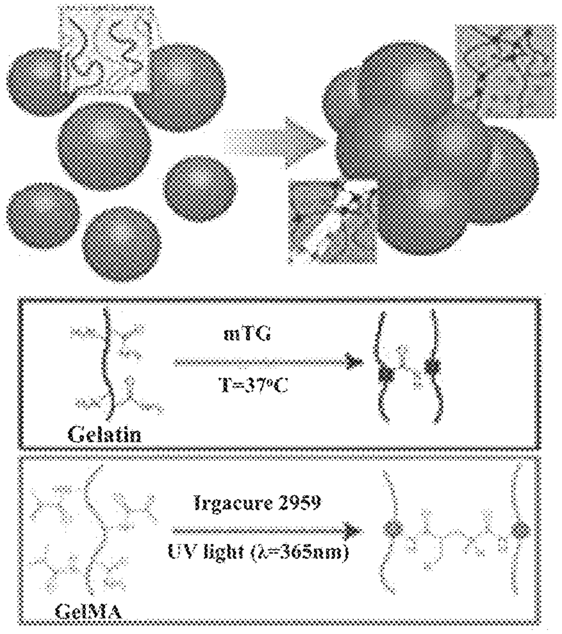
FIG. 25A-E provides a schematic diagram, photomicroscopic images, and graphs of dual-cross-linking of gelatin/GelMA microgels.
Figure 25B:
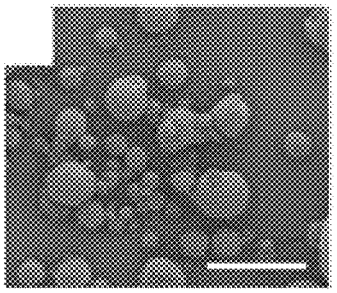
Figure 25C:
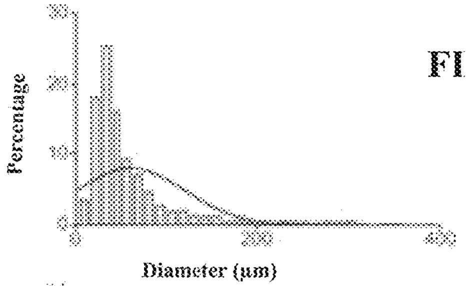
Figure 25D:
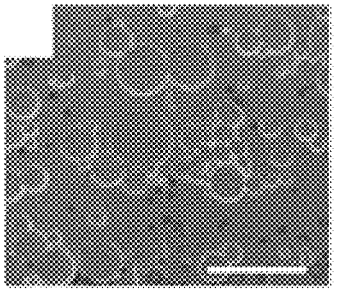
Figure 25E:
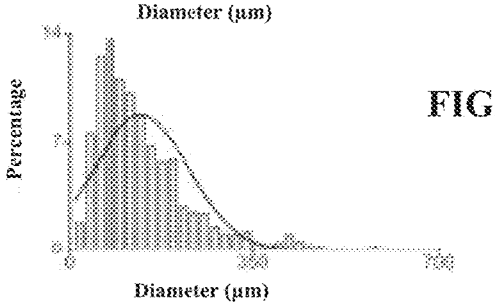
Figure 26:
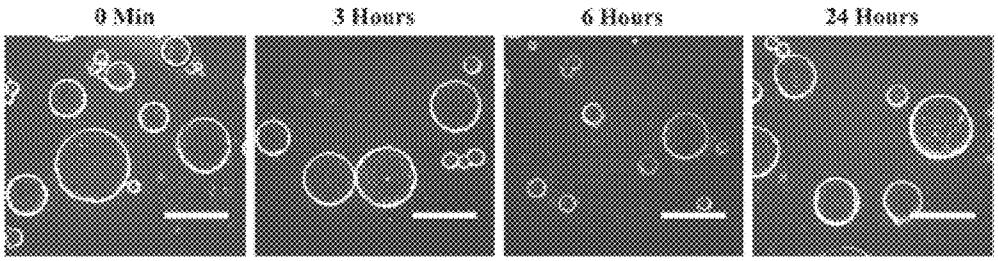
FIG. 26 is a microscopic image illustrating stability of microgels at room temperature at four time points. Scale bar=400 μm.

The gelatin/GelMA microgels were made from a 10% (w/v) aqueous mixture of unmodified gelatin and GelMA (80% substitution) at a 2:1 ratio by weight. A water-in-oil emulsion was created using this solution, which generated physically cross-linked polydisperse microspheres (FIG. 25B-E). The freeze-dried microgels were spherical in shape (FIG. 25B) with an average diameter of 61 (±60) μm (FIG. 25C). When equilibrated in an aqueous environment (FIG. 25D), the average diameter increased to 139 (±90) μm (FIG. 25E). As such, void space between assembled microgels is on the order of tens of microns in size, which allows adequate space for cell encapsulation. Photo-curable microgels from a mixture of unmodified gelatin and GelMA have advantages over GelMA-only microgels, as microgels can be cured also by enzymatic cross-linking, and thermal stability of microgels can be fine-tuned by adjusting the gelatin/GelMA ratio. For example, the microgels that are made by GelMA only (80% substitution) are unstable at room temperature and the curing has to be done using chilled solutions,[18] which is not an ideal condition for in situ cell encapsulation. On the other hand, the microgels that are made of gelatin and GelMA (2:1) are stable in an aqueous solution at room temperature (FIG. 26). This allows cell encapsulation under ambient conditions using these microgels.

The gelatin/GelMA microgels can be cured to form a bulk hydrogel by photopolymerization in the presence of photoinitiator (PI) and the addition of mTG. Rapid curing of the gelatin/GelMA microgels and the stability of the resulting bulk hydrogel were tested by immersing the hydrogels in a warm water bath (45° C.) after 2.5 min of cross-linking (FIG. 27A-D). Immersion in a warm water bath eliminates the effects of physical cross-links among the gelatin chains, so a bulk hydrogel would remain intact only if there were enough covalent cross-links. Experiments were performed using either high PI concentration (0.5%) or low PI concentration (0.05%). PI-induced radicals during photopolymerization are known to be cytotoxic [E. R. Shearier, et al., (2016) ACS Biomater. Sci. Eng., 2, 634-642 and M. O. Wang, et al., (2013) Biomacromolecules, 14, 1321-1329], thus minimizing the PI concentration is important for applications in biological systems.

Figure 27A:
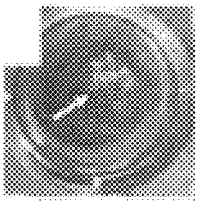
FIG. 27A-D shows stability of the microgel assembly after curing the microgels with UV irradiation only using 0.5% photoinitiator (PI) (FIG. 27A) and 0.05% PI (FIG. 27B); or with mTG and UV irradiation using 0.5% PI (FIG. 27C) or 0.05% PI (FIG. 27D). Arrows indicate the bulk hydrogels.
Figure 27B:
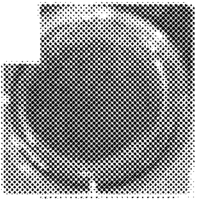
Figure 27C:
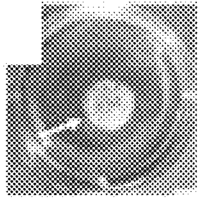
Figure 27D:
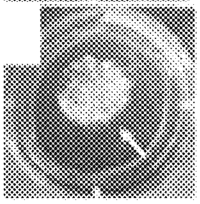
Figure 27E:
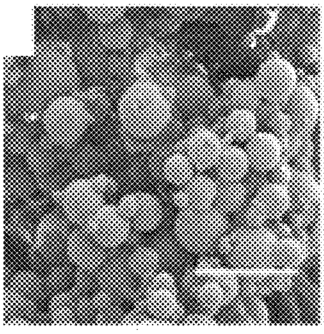
FIG. 27E-F are SEM images of microgels cross-linked by mTG and UV irradiation using 0.5% PI (FIG. 27E) or 0.05% PI (FIG. 27F). Scale bar=200 μm.
Figure 27F:
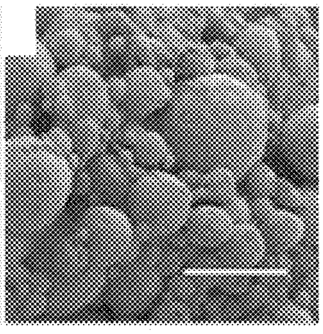

Microgels cured only by mTG dissociated completely after immersion in the warm water bath, indicating that the mTG-based cross-linking was not fast enough to cure the microgels in 2.5 min. When the same microgels were cured under 2.5 min of UV irradiation, a stable bulk hydrogel was formed (FIG. 27A) in the presence of high PI concentration (0.5%). It is attributed to the rapid formation of covalent cross-links within and between microgels by photopolymerization among GelMA chains. However, the microgel assembly completely dissociated when cured in the presence of low PI concentration (FIG. 27B). In this case, photopolymerization alone was insufficient to cure the microgels. In both cases, a more stable hydrogel was formed when microgels were cured by both mTG and UV irradiation (FIG. 27C-D). This shows that dual-cross-linking by UV photopolymerization and mTG allows for rapid curing of the gelatin/GelMA microgels even with a low PI concentration. When viewed by SEM (FIG. 27E-F), hydrogels were clearly made of microspheres, with pores created by the interstitial space.

Figure 27G:
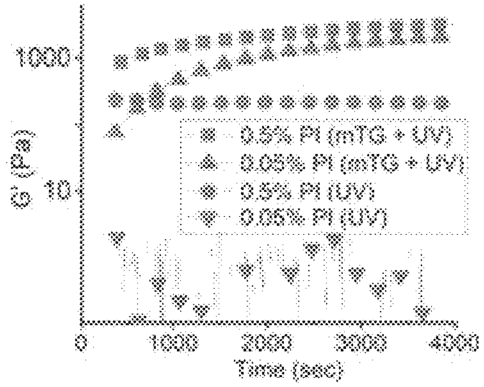
FIG. 27G is a graph showing gelation kinetics of hydrogels formed by either UV irradiation only or mTG and UV irradiation. For the simplicity of the data presentation, only the storage moduli (G') are presented in this figure. The plots of loss moduli and temperature sweep can be found in FIGS. 28 and 29A-O. Results of tissue adhesion tests are shown in FIG. 27H-K. Microgels were injected into 8 mm holes made in porcine cornea and cross-linked for 2.5 min by UV irradiation only using 0.5% PI (FIG. 27H), and 0.05% PI (FIG. 27I); or by mTG and UV irradiation using 0.5% PI (FIG. 27J) and 0.05% PI (FIG. 27K). Scale bar=10 mm.
Figure 28:
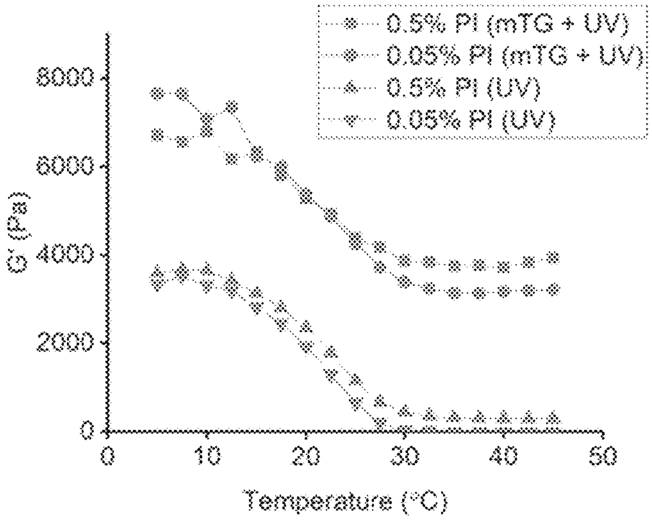
FIG. 28 provides a graph with results of a temperature sweep. Data is presented as means of three independent experiments.
Figure 29A:
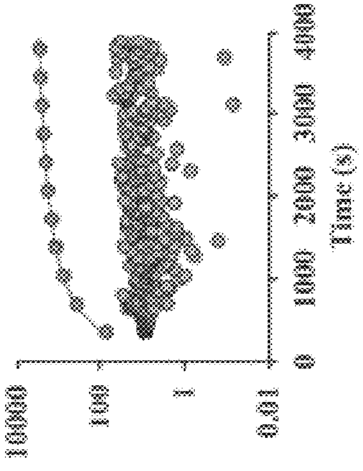
FIG. 29A-O provides graphs illustrates rheology results. The graphs provide representative time, average frequency and temperature sweep for microporous hydrogel using: mTG only (FIG. 29A-C, in all top traces are storage modulus, lower traces are loss modulus); 0.5% PI, UV only (FIG. 29D-F, in FIG. 29D and FIG. 29F top traces are storage modulus and lower traces are loss modulus); 0.5% PI, UV+mTG (FIG. G-I, in all top traces are storage modulus, lower traces are loss modulus); 0.05% PI, UV only (FIG. J-L, FIG. 29L top trace is storage modulus and lower trace is loss modulus); and 0.05% PI, UV+mTG (FIG. 29M-O, in all top traces are storage modulus, lower traces are loss modulus).
Figure 29B:
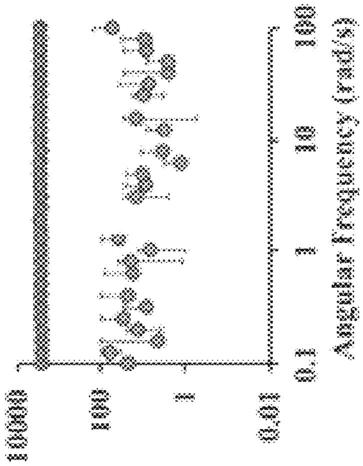
Figure 29C:
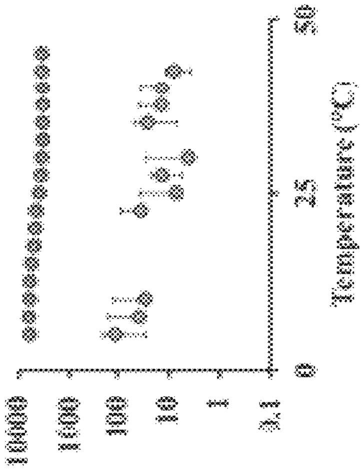
Figure 29D:
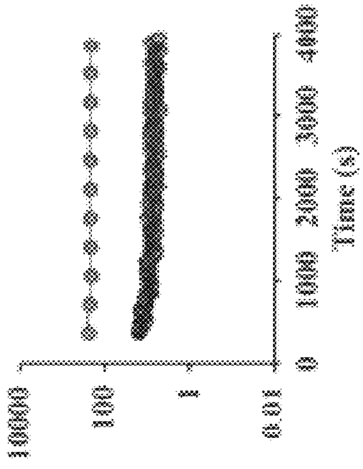
Figure 29E:
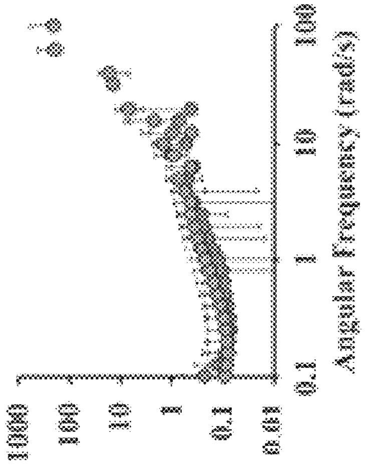
Figure 29F:
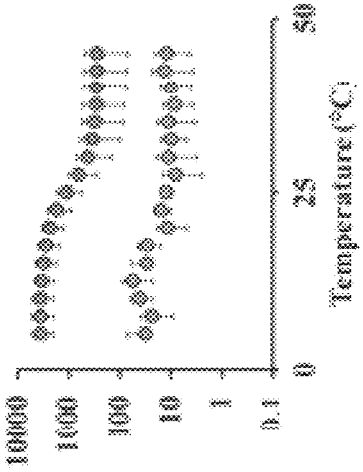
Figure 29G:
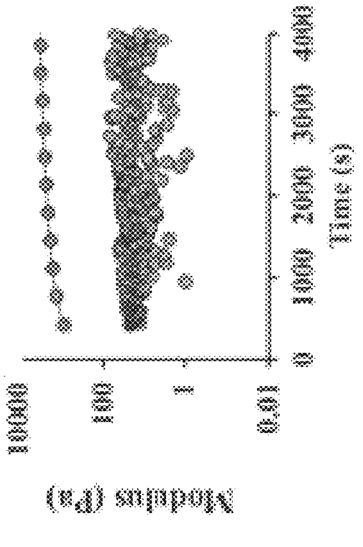
Figure 29H:
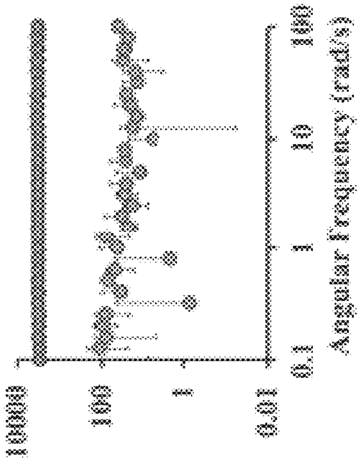
Figure 29I:
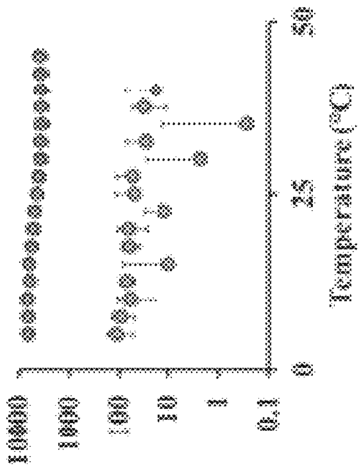
Figure 29J:
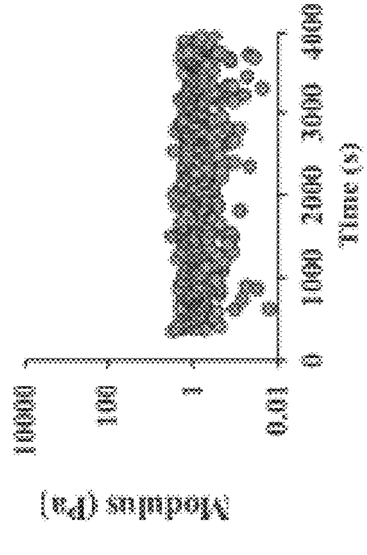
Figure 29K:
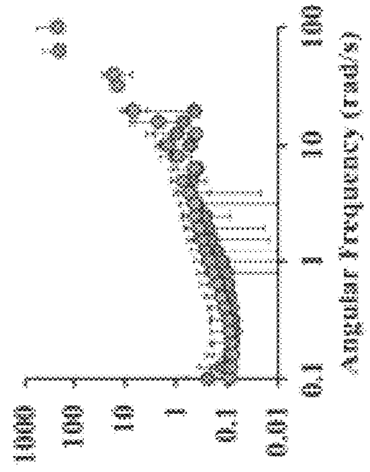
Figure 29L:
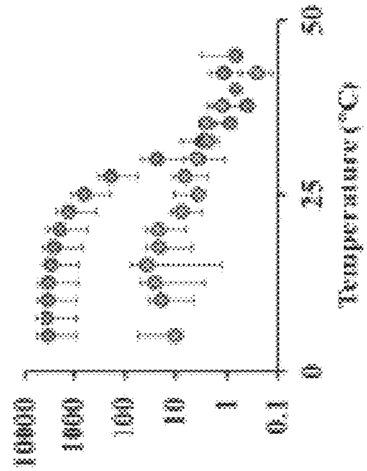
Figure 29M:
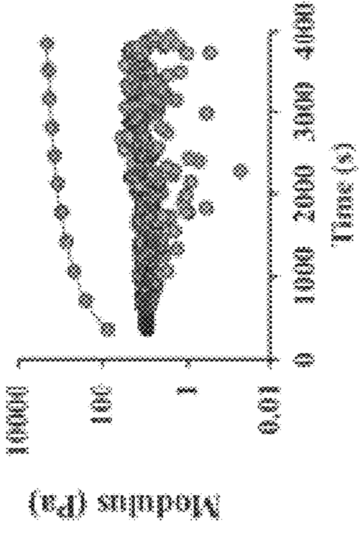
Figure 29N:
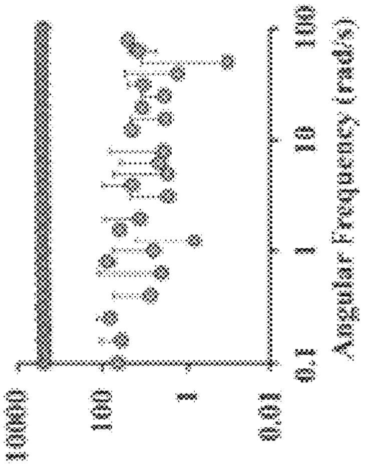
Figure 29O:
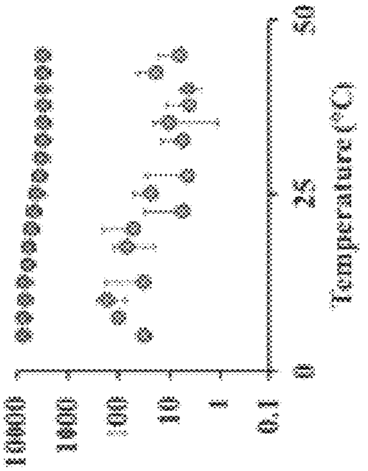

Gelation kinetics and viscoelastic properties of the hydrogels were quantified by rheology (FIG. 27G, FIG. 28, and FIG. 29). UV irradiation with a high PI concentration (0.5%) rapidly increased G', but there were minimal changes after removal of the UV source. The combination of both curing methods (mTG+UV) resulted in a rapid increase of G' and a much stiffer hydrogel than the one cured by UV only, which can be attributed to the additional covalent cross-links formed by mTG. The effect of UV irradiation was much reduced when a low PI concentration (0.05%) was used, and cross-linking by UV irradiation alone did not form a stable hydrogel. When both curing methods were combined (mTG+UV), the microgels quickly formed a stable gel, although G' was lower at all time points when compared to the corresponding case of high PI concentration.

Temperature sweep provides further information about the nature of cross-links within hydrogels [A. I. Van Den Bulcke, et al., (2000) Biomacromolecules, 1, 31-38]. For both PI concentrations, G' decreased for all curing methods as temperature increased, which is characteristic of physically cross-linked gelatin hydrogels (FIG. 29). For the case of mTG+UV, G' settled at 3500-4000 Pa above 30° C., which verifies the presence of covalent cross-links within the hydrogels which do not dissociate at high temperatures. When the microgels were cured by UV irradiation only, G' settled at much lower values. A higher PI concentration resulted in higher G' at 45° C. (284+/−214 Pa for high PI concentration vs 0.70+/−2.5 Pa for low PI concentration), indicating that photopolymerization became more efficient as the PI concentration increased.

In addition to rapid curing, adhesion of the resulting hydrogel to the applied tissue is an important feature to make this injectable formulation more clinically useful [G. D. Nicodemus & S. J. Bryant, (2008) *Tissue Eng. Part B Rev.,* 14, 149-165; D. A. Wang, et al., (2007) *Nat. Mater.,* 6, 385-392; and D. Seliktar, (2010) *Science,* 336, 1124-1128]. Previous experiments demonstrated that the microporous hydrogel made by assembly of gelatin microgels adhered to porcine corneal tissue within 1 hour by the action of mTG [S. Hou, et al., (2018) ACS Appl. Bio Mater., 2018, 1, 1430-1439]. mTG has been used as a tissue adhesive and is considered biocompatible [M. K. McDermott, et al., (2004) Biomacromolecules, 5, 1270-1279 and T. N. Dinh, et al., (2018) ACS Biomater. Sci. Eng., 2018, 4, 3471-3477]. Porcine cornea was used as a model tissue due to having rich collagen content and ready availability. mTG-catalyzed tissue adhesion was examined when used in conjunction with photopolymerization. The microgels were injected into an 8 mm hole in a porcine cornea and allowed to cross-link by UV irradiation alone or by both mTG cross-linking and UV irradiation (mTG+UV). After curing, the cornea-hydrogel construct was immersed and shaken in a warm water bath (45° C.) (FIG. 27H-K).

Figure 27H:
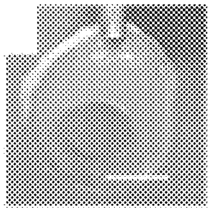
FIG. 27 provides microscopic images and a graph showing characterization of microgel assembly.
Figure 27I:
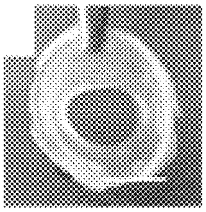
Figure 27J:
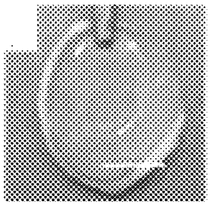
Figure 27K:
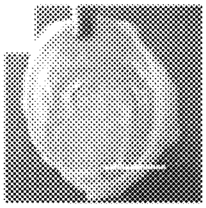

For high PI concentration, UV irradiation created a stable hydrogel, but it readily detached from the tissue when immersed in the warm water bath (FIG. 27H). When the low PI concentration was used, the UV irradiation alone did not form a bulk hydrogel, precluding tissue adhesion (FIG. 27I). When mTG was added in addition to UV irradiation, not only did a stable hydrogel form (FIG. 27B and FIG. 27D), but the resulting hydrogel also adhered to the cornea tissue with both PI concentrations (FIG. 27J-K). These results clearly showed the dual-cross-linking by mTG and photopolymerization achieved rapid curing of the gelatin/GelMA microgels and the resulting hydrogel stably adhered to tissue even at low PI concentration (0.05%). The results also showed that photopolymerization alone does not allow the tissue adhesion of the microgel-based hydrogel even at a high PI concentration (0.5%).

Two independent factors contribute to stable adhesion of a hydrogel to a wet tissue surface—interfacial adhesion (i.e. cross-linking between the hydrogel and tissue) and cohesion (i.e. mechanical strength of the hydrogel). The rapid and stable tissue adhesion of the microgel-based hydrogel was attributed to the simultaneous enhancement of both interfacial adhesion (by mTG) and cohesion (by UV) enabled by the dual-cross-linking approach.

Figure 30:
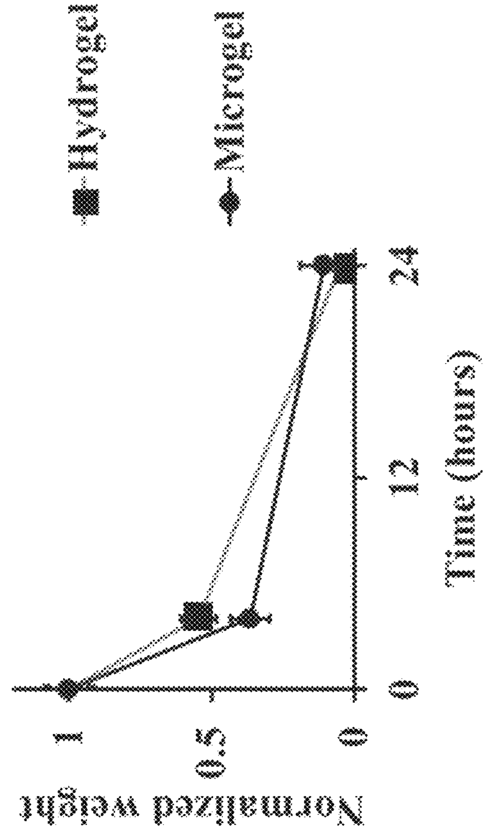
FIG. 30 provides a graph showing degradation of gelatin/GelMA microgels and hydrogel. The error bars represent standard deviations (n=3).

Enzymatic degradation of gelatin/GelMA microgels and the hydrogel made of these microgels was measured using collagenase type II (FIG. 30) as previously described [S. R. Shin, et al., (2013) *Adv. Mater.,* 2013, 25, 6385-6391]. Both microgels and the hydrogel cross-linked by both mTG and UV degraded completely within 24 hours, demonstrating the biodegradability of this formulation. This result is consistent with the fact that gelatin and GelMA, a gelatin derivative, has been shown to be degraded both in vitro and in vivo by various enzymes [S. Hou, et al., (2018) *ACS Appl. Bio Mater.,* 2018, 1, 1430-1439 and M. Zhu, Y. et al., (2019) *Sci. Rep.,* 9, 6863].

In situ cell encapsulation in a hydrogel is an important technology for the delivery of viable cells for wound healing and regenerative medicine [J. Koh, et al., (2019) Small, 15, 903147; R. Dimatteo, et al., (2018) Adv. Drug Deliv. Rev., 127, 167-184; V. X. Truong, et al., (2015) J. Am. Chem. Soc., 137, 1618-1622; and Z. Mũnoz, et al., (2014) Biomater. Sci., 2, 1063-1072]. The feasibility of using the microgel-based injectable hydrogel for cell delivery was investigated using human dermal fibroblasts (hDFs) (FIG. 31, FIG. 32, and FIG. 33). Unlike most hydrogel systems in which cells are homogeneously distributed in the hydrogel phase, cells are encapsulated in the interstitial space between microgels.

Figure 31A:
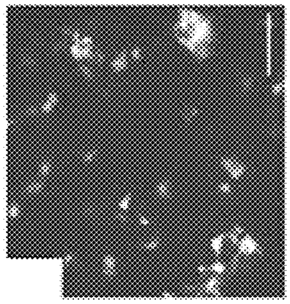
FIG. 31A-F provides photomicrographs and graphs showing results of studies included cell encapsulating constructs.
Figure 31B:
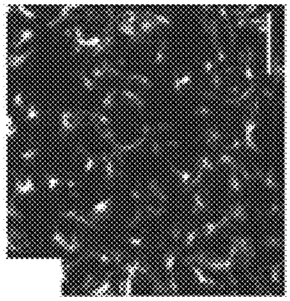
Figure 31C:
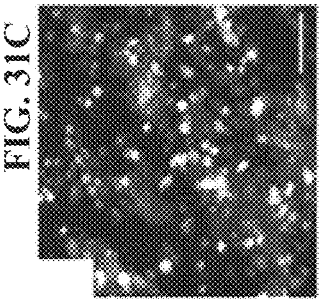

Cell-encapsulating constructs were formed by curing the microgels by both mTG and UV irradiation using either 0.5% PI or 0.05% PI. For a comparison, cells were also encapsulated in a nonporous hydrogel, which was formed by cross-linking a homogeneous mixture of gelatin and GelMA using mTG and UV irradiation (with 0.05% PI). At all time points (day 1 and day 7 post encapsulation), cell viability was high for all groups (FIG. 31A-F, FIG. 33A), although the porous hydrogel with 0.5% PI resulted in the lowest viability on day 1 (p>0.05). Strikingly, the cells encapsulated in the microporous hydrogels exhibited fully spread morphologies as early as day 1 post encapsulation (FIGS. 31A-B and G). This rapid spreading of encapsulated cells, which is attributed to the presence of unrestricted void space within the porous hydrogels, is distinct from most nonporous hydrogels in which the encapsulated cells are trapped by the polymer chains and cannot spread immediately (FIG. 31C).

Cell spreading is an important phenomenon particularly in stem cell differentiation. For example, osteogenic differentiation of mesenchymal stem cells (MSCs) is known to be enhanced with a larger cell spread area in various 2D cultures [R. McBeath, et al., (2004) Dev. Cell, 2004, 6, 483-495 and Y. Yang, et al., (2019) Sci. Rep., 2019, 9, 6891]. In the case of 3D hydrogels, fast stress-relaxation of the polymer chains, which allows the spreading of the encapsulated MSCs, results in enhancement of osteogenic differentiation [O. Chaudhuri, et al., (2016) Nat. Mater., 2016, 15, 326-334]. Therefore, the current injectable formulation which induces rapid spreading of the encapsulated cells will be useful when differentiation of the encapsulated stem cells into a specific lineage (e.g. osteogenic) is desired.

Figure 31D:
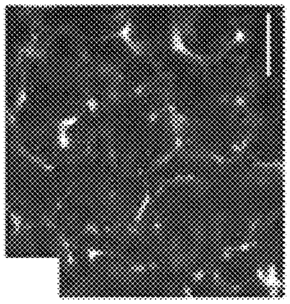
Figure 31E:
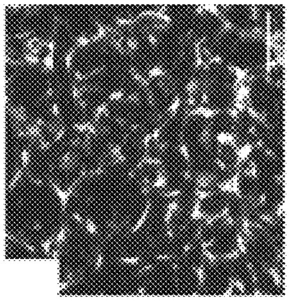
Figure 31F:
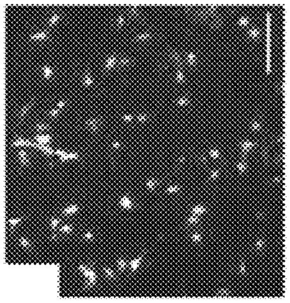
Figure 31G:
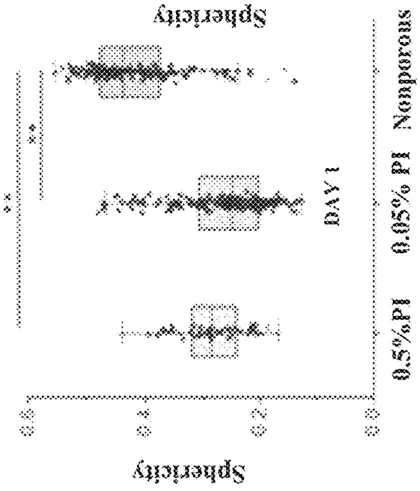
FIG. 31G-H shows results of studies of sphericity of encapsulated cells on day 1 (FIG. 31G) and day 7 (FIG. 31H) post encapsulation.
Figure 31H:
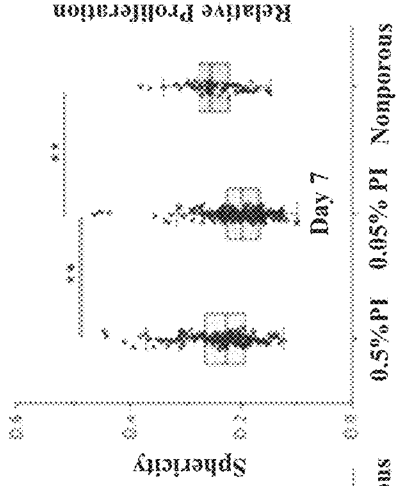
Figure 31I:
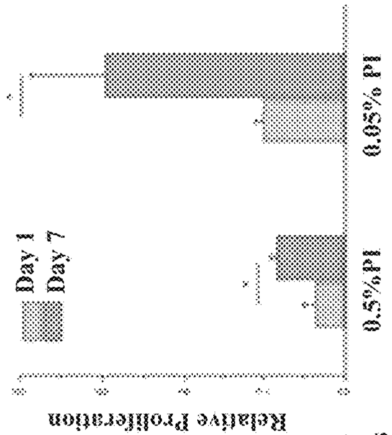
FIG. 31I is a bar graph showing cell proliferation in the microporous hydrogels relative to the nonporous control (n=3). $*p<0.05$ and $**p<0.001$ FIG. 32A-F provides 3 Dimensional representations of live/dead images. Results from days 1 (32A-C) and 7 (FIG. 32D-F) post encapsulation. Shown are hDFs encapsulated in the (a, d) microporous hydrogels made using 0.5% PI (FIGS. 32A & D), microporous hydrogels made with 0.05% PI (FIGS. 32B & E), and nonporous hydrogels made with 0.05% PI (FIGS. 32C & F). Results distinguished between living and dead.
Figure 34A:
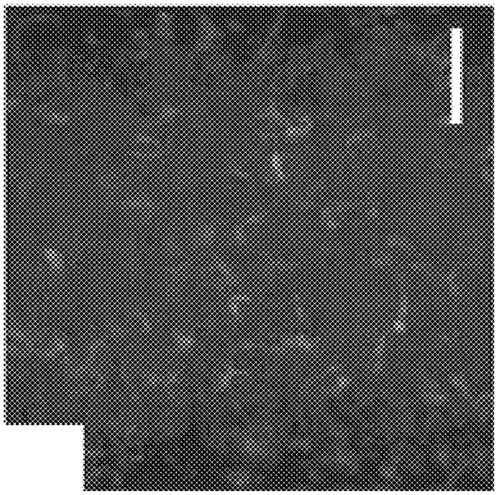
FIG. 34A-F provides photomicroscopic images of encapsulated cells. Actin cytoskeleton (FIG. 34A-C) and cell nuclei (FIG. 34D-F) of the encapsulated cells on day 7. Microporous hydrogel with 0.5% (FIGS. 34A & D) or 0.05% PI (FIGS. 34B & E); nonporous hydrogel with 0.05% PI (FIGS. 34C & F). Actin cytoskeleton was stained with red fluorescence, and cell nuclei were stained with blue fluorescence. There was significant non-specific blue staining of the microgels, but the cell nuclei could still be visualized. Scale bar=200 μm.
Figure 34B:
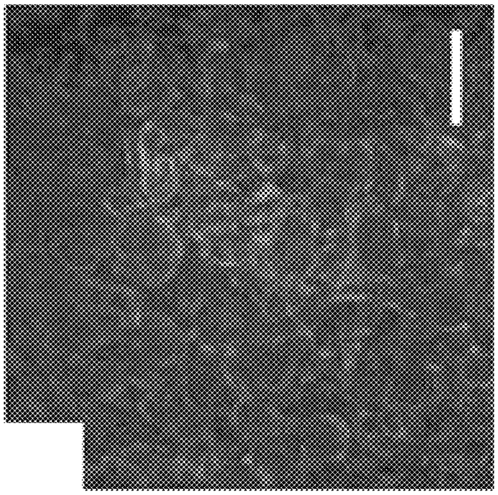
Figure 34C:
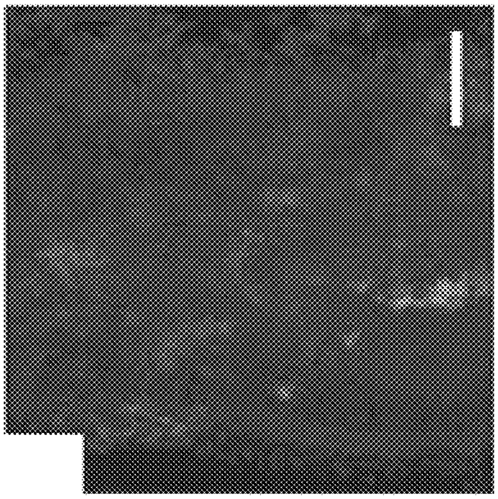
Figure 34D:
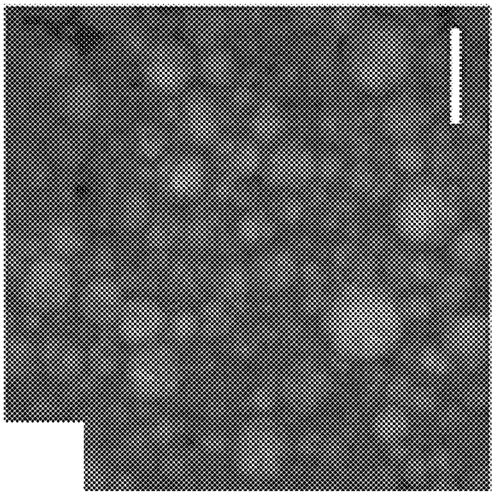
Figure 34E:
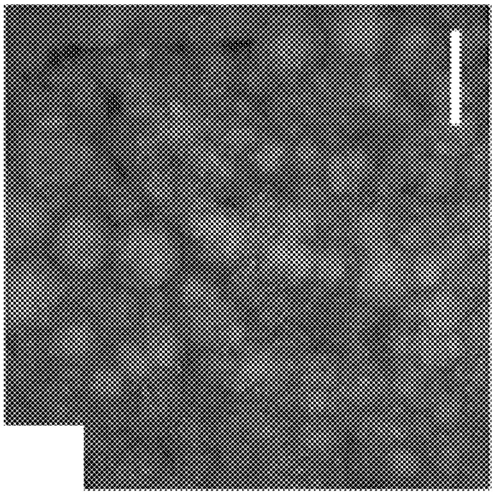
Figure 34F:
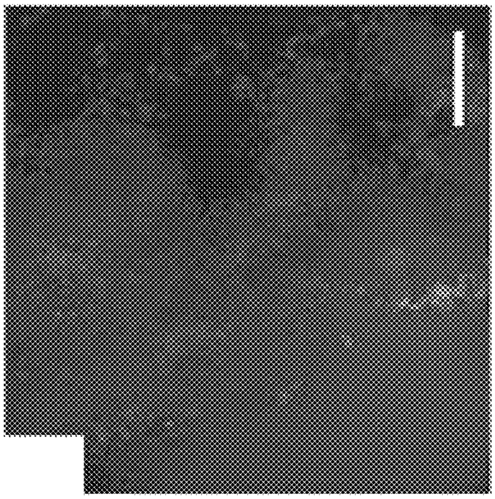

The advantage of encapsulating cells in the pores of the microgel-assembly was further proven by the live/dead assay performed on day 7 post encapsulation (FIG. 31D-F). As on day 1, the cells were well-spread around the microgels within the interstitial space, resulting in decreased sphericities compared to day 1 (FIG. 31H). The cells encapsulated in the nonporous hydrogel still exhibited higher sphericity likely because some cells were still trapped in the polymer mesh. The detailed structures of actin cytoskeleton on day 7 confirmed these results, (FIG. 34).

The benefit of lowering the PI concentration for curing by dual cross-linking mechanism is highlighted by the proliferation. At both time points, the samples with 0.05% PI concentration resulted in higher proliferation than the samples with 0.5% PI concentration (FIG. 31I), presumably due to decreased exposure of cells to free radicals during encapsulation. This result is supported by the significant increase in cytotoxicity on day 1 for the 0.5% PI group measured by lactate dehydrogenase (LDH) release (FIG. 33B). By day 7, LDH release was substantially lower for both groups, indicating the lower proliferation of the 0.5% PI group resulted from the initial cytotoxicity during the photopolymerization. For both PI concentrations, proliferation on day 7 was higher than the cells encapsulated in the nonporous hydrogels, which is consistent with the recent report that MSCs encapsulated in the microporous hydrogel exhibited significantly higher proliferation than the cells encapsulated in the nonporous hydrogel in vivo [J. Koh, et al., (2019) Small, 15, 1903147].

Conclusion—Example 16

Overall, the injectable hydrogel formulation described here has 5 major advantages compared to previously reported injectable hydrogels: (1) enhanced thermal stability of microgels allows for more favorable conditions during cell encapsulation; (2) rapid gelation (2.5 min) under UV irradiation even at a low PI concentration (0.05%) was achieved due to the synergistic actions of UV photopolymerization and mTG-based enzymatic cross-linking; (3) the use of low PI concentration results in high viability and proliferation of the encapsulated cells; (4) due to the action of mTG in conjunction with UV photopolymerization, the hydrogel can adhere to the target tissue stably within 2.5 min; (5) the presence of pores allows rapid adhesion, spreading, and proliferation of the encapsulated cells. The results demonstrated that this novel formulation will have many applications related to accelerated wound healing and cell delivery-based therapeutics.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles “a” and “an,” as used herein in the specification and in the claims, unless clearly indicated to the contrary, should be understood to mean “at least one.” The phrase “and/or,” as used herein in the specification and in the claims, should be understood to mean “either or both” of the elements so conjoined, i.e., elements that are conjunctively present in some cases and disjunctively present in other cases. Other elements may optionally be present other than the elements specifically identified by the “and/or” clause, whether related or unrelated to those elements specifically identified, unless clearly indicated to the contrary.

All references, patents and patent applications and publications that are cited or referred to in this application are incorporated by reference in their entirety herein.

Although the present disclosure has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true spirit and scope of the present disclosure.

What is claimed is:

1. A method for producing a porous hydrogel, the method comprising:

preparing gelatin/gelatin methacrylate (GelMA) microgels comprising gelatin and GelMA, wherein the gelatin/GelMA microgels have an average diameter between 130 μm and 250 μm when in a hydrated state;

preparing a microgel solution comprising the gelatin/GelMA microgels, cross-linking enzyme comprising transglutaminase, and photoinitiator present at a concentration range of 0.001% to 0.1% (w/v) to minimize cytotoxic effects on live cells; and curing the microgel solution by contacting the gelatin/GelMA microgels with ultraviolet (UV) light for a time effective for the photoinitiator to activate cross-linking of the gelatin/GelMA microgels, to produce a porous hydrogel having a porosity sufficient for cell migration and proliferation in the interstitial space of the porous hydrogel.

2. The method of claim 1, wherein the transglutaminase is microbial transglutaminase (mTG).

3. The method of claim 1, wherein curing the microgel solution comprises incubating the microgel solution at about 37° C.

4. The method of claim 1, wherein the photoinitiator comprises at least one of Irgacure 2959, vitamin B12, and lithium phenyl-2,4,6-trimethylbenzoylphosphinate (LAP).

5. The method of claim 1, further comprising: preparing the microgel solution to further comprise one or more live cells.

6. The method of claim 5, wherein the one or more live cells comprise one or more stem cells.

7. A microgel solution, comprising:

(a) gelatin/gelatin methacrylate (GelMA) microgels comprising gelatin and GelMA, wherein the gelatin/GelMA microgels have an average diameter between 130 μm and 250 μm, the average diameter of the microgels being sufficient to create an interstitial space in a resulting hydrogel of sufficient porosity for cell migration and proliferation;

(b) cross-linking enzyme comprising transglutaminase; and (c) photoinitiator present at a concentration range of 0.001% to 0.1% (w/v) to minimize cytotoxic effects on live cells.

8. The microgel solution of claim 7, wherein the cross-linking enzyme further comprises one or more of genipin, factor XIIIa and horse radish peroxidase (HRP).

9. The microgel solution of claim 7, further comprising an antioxidant agent.

10. The microgel solution of claim 7, further comprising one or more live cells.

11. A method of delivering one or more live cells into a subject, the method comprising:

(a) preparing a microgel solution comprising:

gelatin/gelatin methacrylate (GelMA) microgels comprising gelatin and GelMA, wherein the gelatin/GelMA microgels have an average diameter between 130 μm and 250 μm, (ii) cross-linking enzyme comprising transglutaminase, (iii) photoinitiator present at a concentration range of 0.001% to 0.1% (w/v) to minimize cytotoxic effects on live cells, and (iv) one or more live cells;

(b) administering the microgel solution to a target in a subject where the one or more live cells are intended to be delivered to the subject; and (c) curing the microgel solution by contacting the gelatin/GelMA microgels with ultraviolet (UV) light for a time effective for the photoinitiator to activate cross-linking of the gelatin/GelMA microgels, to produce a porous hydrogel that is adhered by transglutaminase cross-linking to the target and having a porosity sufficient for cell migration and proliferation of the one or more live cells in the interstitial space of the porous hydrogel.

12. The method of claim 11, wherein the one or more live cells comprise one or more stem cells.

13. The microgel solution of claim 7, wherein the microgel solution comprises 0.05% (w/v) concentration of the photoinitiator.

14. The microgel solution of claim 7, where the transglutaminase is microbial transglutaminase (mTG).

15. The method of claim 11, where the transglutaminase is microbial transglutaminase (mTG).

16. The method of claim 1, wherein the gelatin/GelMA microgels are prepared from lyophilized gelatin/GelMA microgels.

17. The microgel solution of claim 7, wherein the gelatin/GelMA microgels are hydrated from lyophilized gelatin/GelMA microgels.

18. The method of claim 11, wherein, the gelatin/GelMA microgels are prepared from lyophilized gelatin/GelMA microgels.

19. The microgel solution of claim 7, wherein the microgel solution comprises 0.02% to 0.08% (w/v) concentration of the photoinitiator.

20. The method of claim 7, wherein the microgel solution comprises 0.02% to 0.08% (w/v) concentration of the photoinitiator.

* * * * *

UNITED STATES PATENT AND TRADEMARK OFFICE

CERTIFICATE OF CORRECTION

PATENT NO. : 11,998,658 B2
APPLICATION NO. : 16/786312
DATED : June 4, 2024
INVENTOR(S) : Kyung Jae Jeong It is certified that error appears in the above-identified patent and that said Letters Patent is hereby corrected as shown below:

In the Claims

In Claim 11, Column 32, Line 6, delete “gelatin/gelatin methacrylate” and insert -- (i) gelatin/gelatin methacrylate --.

Signed and Sealed this
Third Day of December, 2024

Katherine Kelly Vidal

*Director of the United States Patent and Trademark Office*